United States Patent
Venkatraman et al.

(10) Patent No.: US 12,370,201 B2
(45) Date of Patent: Jul. 29, 2025

(54) LIPOSOMAL FORMULATIONS OF CORTICOSTEROIDS AND USES THEREOF

(71) Applicant: EDEN Opthalmic PTE Ltd., Singapore (SG)

(72) Inventors: Subramanian Venkatraman, Palo Alto, CA (US); Chee Wai Wong, Singapore (SG); Tina Howden, Singapore (SG)

(73) Assignee: EDEN Ophthalmic PTE Ltd., Singapore (SG)

( * ) Notice: Subject to any disclaimer, the term of this patent is extended or adjusted under 35 U.S.C. 154(b) by 0 days.

(21) Appl. No.: 18/768,689

(22) Filed: Jul. 10, 2024

(65) Prior Publication Data
US 2025/0017945 A1 Jan. 16, 2025

Related U.S. Application Data

(60) Provisional application No. 63/512,876, filed on Jul. 10, 2023.

(51) Int. Cl.
*A61K 31/573* (2006.01)
*A61K 9/00* (2006.01)
*A61K 9/1271* (2025.01)

(52) U.S. Cl.
CPC .......... *A61K 31/573* (2013.01); *A61K 9/0048* (2013.01); *A61K 9/1271* (2013.01)

(58) Field of Classification Search
CPC ... A61K 31/573; A61K 9/0048; A61K 9/1271
See application file for complete search history.

(56) References Cited

U.S. PATENT DOCUMENTS

| | | |
|---|---|---|
| 9,114,070 B2 | 8/2015 | Hara et al. |
| 9,956,195 B2 | 5/2018 | Venkatraman et al. |
| 10,272,040 B2 | 4/2019 | Venkatraman et al. |
| 10,471,010 B2 | 11/2019 | Metselaar |
| 11,672,784 B2 | 6/2023 | Venkatraman et al. |
| 11,684,570 B2 | 6/2023 | Liegner et al. |
| 2004/0224010 A1 | 11/2004 | Hofland et al. |
| 2011/0033468 A1 | 2/2011 | Shih et al. |
| 2017/0042809 A1* | 2/2017 | Yu .................. A61K 31/433 |
| 2018/0042765 A1* | 2/2018 | Noronha ............... A61P 43/00 |
| 2019/0151236 A1 | 5/2019 | Metselaar et al. |
| 2020/0188405 A1 | 6/2020 | Kaushal |
| 2023/0263780 A1 | 8/2023 | Venkatraman et al. |

FOREIGN PATENT DOCUMENTS

WO WO-2017184080 A1 10/2017

OTHER PUBLICATIONS

Gaballa et al, "Corticosteroids in ophthalmology: drug delivery innovations, pharmacology, clinical applications, and future perspectives", Drug Deliv Trans Res, 2021, vol. 11, pp. 866-893. (Year: 2021).*

(Continued)

*Primary Examiner* — Benjamin J Packard
*Assistant Examiner* — Joshua A Atkinson
(74) *Attorney, Agent, or Firm* — COOLEY LLP

(57) ABSTRACT

The present disclosure provides ophthalmic compositions comprising a steroid, such as prednisolone encapsulated in a liposomal carrier and methods of use thereof.

16 Claims, 5 Drawing Sheets

(56) References Cited

OTHER PUBLICATIONS

Hombrebueno et al., "Intravitreal Injection of Normal Saline Induces Retinal Degeneration in the C57BL/6J Mouse", Transl Vis Sci Tech, 2014, 3(2): 3, pp. 1-9. (Year: 2014).*
International Search Report and Written Opinion for PCT Application No. PCT/US2024/037386 mailed Sep. 6, 2024, 14 pages.
Leibowitz et al., "Antiinflammatory medications". Int Ophthalmol Clin. 1980 Fall;20(3):117-34.
Sousa "The bioavailability and therapeutic effectiveness of prednisolone acetate vs. prednisolone sodium phosphate: a 20-year review". CLAO J. Oct. 1991;17(4):282-4.
Wong et al., "Evaluation of subconjunctival liposomal steroids for the treatment of experimental uveitis". Scientific reports. Apr. 26, 2018; 8(1): 11 pages.

* cited by examiner

LIPOSOMAL FORMULATIONS OF CORTICOSTEROIDS AND USES THEREOF

CROSS REFERENCE TO RELATED APPLICATIONS

This application claims the benefit of priority under 35 U.S.C. 119 (e) to U.S. Provisional Patent Application No. 63/512,876, filed Jul. 10, 2023, the disclosure of which is incorporated herein by reference in its entirety.

BACKGROUND

Steroids, for example corticosteroids, are utilized to treat a wide variety of ophthalmic diseases that affect the posterior segment of an eye. Examples of diseases treated with corticosteroids include central retinal vein occlusion (CRVO), branch retinal vein occlusion (BRVO), choroidal macular edema (CME), diabetic macular edema (DME), diabetic macular retinopathy, uveitis, telangitis, and age related macular degeneration (ARMD) as well as other diseases or conditions of the eye, for example of the posterior segment of the eye.

Epidemiologic studies have shown that approximately 1 in 3 persons with diabetes mellitus has Diabetic Retinopathy (DR). Based on these rates, between 100 million and 120 million people have DR worldwide. The prevalence rate for retinopathy for all adults with diabetes aged 40 and older in the United States is 28.5% (4.2 million people); worldwide, the prevalence rate has been estimated at 34.6% (93 million people). Rates in the U.S. expected to double from 7.7 million in 2010 to 14.6 million in 2050. In the U.S. prevalence is 0.6 percent for BRVO and 0.1 percent for CRVO and is highest inpatients>80 years old (4.6%).

There is a need for new ophthalmic compositions comprising steroids and their use for treating ophthalmic conditions of eyes.

SUMMARY

In embodiments, the present disclosure provides ophthalmic compositions comprising a steroid, such as prednisolone encapsulated in a liposomal carrier comprising an unsaturated phospholipid e.g., mono-unsaturated or di-unsaturated phospholipid.

In embodiments, the unsaturated phospholipid is a phosphatidylcholine.

In embodiments, the unsaturated phospholipid is 1-palmitoyl-2-oleoyl-glycero-3-phosphocholine (16:0-18:1 PC; (POPC)) or 1,2-dioleoyl-sn-glycero-3-phosphocholine (18:1 (Δ9-Cis) PC; (DOPC).

In embodiments, the loading of prednisolone is at least about 3% w/w of the liposomal carrier.

In embodiments, the ophthalmic compositions exhibit an in vitro release profile wherein 50% or less of prednisolone is released after about 12 hours and about 65% or less prednisolone is released after about 24 hours.

In embodiments, leakage of prednisolone from liposomal carriers is less than about 5%, less than about 10%, less than about 15%, less than about 20%, less than about 30% or less than about 40% when stored over 3 weeks at 5° C.

In embodiments, the present disclosure provides an ophthalmic composition comprising:
 a steroid encapsulated in a liposome comprising an unsaturated phospholipid,
 wherein the liposome composition exhibits an in vitro release profile wherein 50% or less of prednisolone is released after about 12 hours and about 65% or less prednisolone is released after about 24 hours.

In embodiments, the ophthalmic compositions of the present disclosure are a pharmaceutical formulation for injection; for example, intraocular injection, intravitreal injection or subconjunctival injection.

In embodiments, the present disclosure provides methods for treating inflammation of the eye in a subject in need thereof, comprising administering an ophthalmic composition of the present disclosure.

In embodiments, the present disclosure provides methods for treating macular edema in a subject in need thereof, comprising administering an ophthalmic composition of the present disclosure.

DEFINITIONS

Figure 1:
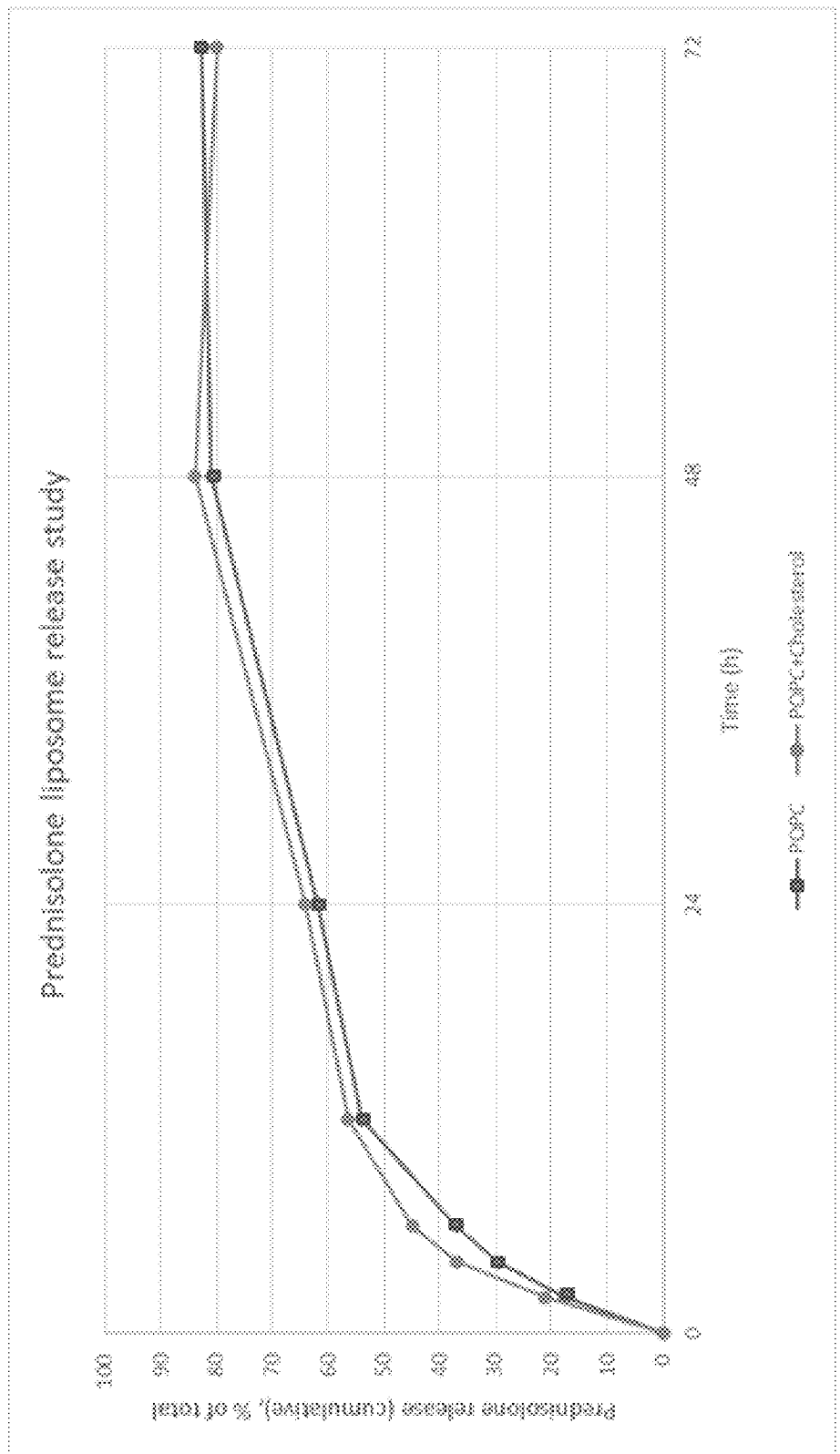
FIG. 1 shows release of prednisolone from POPC liposomes at 37° C., 72 hours.

Listed below are definitions of various terms used in the specification and claims to describe the present disclosure. Unless defined otherwise, all technical and scientific terms used in this disclosure have the same meanings as commonly understood by one of ordinary skill in the art to which this disclosure belongs.

The term "about" when immediately preceding a numerical value means a range (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. For example in a list of numerical values such as "about 49, about 50, about 55, . . . ", "about 50" means a range extending to less than half the interval(s) between the preceding and subsequent values, e.g., more than 49.5 to less than 50.5. Furthermore, the phrases "less than about" a value or "greater than about" a value should be understood in view of the definition of the term "about" provided herein. Similarly, the term "about" when preceding a series of numerical values or a range of values (e.g., "about 10, 20, 30" or "about 10-30") refers, respectively to all values in the series, or the endpoints of the range.

The term "phospholipid" refers to a class of lipids comprising a hydrophilic "head" containing a phosphate group and two hydrophobic "fatty acid tails" derived from fatty acids, joined by an alcohol residue (usually a glycerol molecule). The phosphate group may be further bound to hydrogen, choline, serine, ethanolamine, or inositol, thus, diversifying into phosphatidic acid, phosphatidylcholine, phosphatidylserine, phosphatidylethanolamine, and phosphatidylinositol phospholipids, respectively.

As used herein, an "ocular disease or disorder" is a disease or disorder which affects or involves the eye or one of the parts or regions of the eye. For example, posterior ocular disease or disorder is a disease or disorder which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

DETAILED DESCRIPTION

Throughout this disclosure, various patents, patent applications and publications are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

Diabetic Macular Edema is a chronic inflammatory condition in the back of the eye, that can lead eventually to retinopathy and blindness, if not controlled at an early stage. The inflammatory condition is triggered by hyperglycemia, leading to cytokine release from retinal endothelial cells, and further recruitment of macrophages and monocytes that are a result of a leaking blood-retinal barrier which progresses to a chronic inflammatory state. Treating DME with a single injection of a naked steroid may suppress the initial inflammatory cascade but will not prevent further activation of macrophages leading to continued vascular leakage and inflammation. Conversely, a slow-releasing formulation such as OZURDEX® (dexamethasone intravitreal implant), does not release a bolus; any improvement in DME is seen only after 1 month of implantation.

Parameters to consider when formulating therapeutic agents e.g., for the treatment of ocular diseases or disorders include rate and extent of drug release from the formulation, drug loading, stability of the formulation and duration of drug release time. However, achieving a formulation which optimizes each these components/factors is difficult to achieve in practice.

It would be advantageous to provide steroid formulations suitable for injection to treat the ocular diseases such as DME, which minimize the frequency of injections (as repeated injections can lead to retinal detachment) and maximize localized effects, such as macrophage uptake and suppression.

The liposomal formulations of the present disclosure address these problems. Without being bound by theory, administration of the liposomal formulations of the present disclosure release a bolus amount of steroid in the first 12-24 hours to suppress the initial inflammatory cascade. Subsequent de-activation of macrophages occurs over several days by virtue of uptake of these liposomal nanoparticles by the macrophages.

Compositions

In embodiments, the present disclosure provides ophthalmic compositions comprising a steroid encapsulated in a liposomal carrier.

Liposomal carriers of the present disclosure may comprise an unsaturated phospholipid, such as, a mono-unsaturated or di-unsaturated phospholipid. In embodiments, the unsaturated phospholipid is a mono-unsaturated phospholipid. In embodiments, the unsaturated phospholipid is a di-unsaturated phospholipid.

In embodiments, the unsaturated phospholipid is present in an amount of about 1%-95% or more by weight of liposomal carrier, including from about 1% by weight, about 2% by weight, about 3% by weight, about 4% by weight, about 5% by weight, about 6% by weight, about 7% by weight, about 8% by weight, about 9% by weight, about 10% by weight, about 11% by weight, about 12% by weight, about 13% by weight, about 14% by weight, about 15% by weight, about 16% by weight, about 17% by weight, about 18% by weight, about 19% by weight, about 20% by weight, about 25% by weight, about 30% by weight, about 35% by weight, about 40% by weight, about 45% by weight, about 50% by weight, about 55% by weight, about 60% by weight, about 65% by weight, about 70% by weight, about 75% by weight, about 80% by weight, about 85% by weight, about 90% by weight, about 95% by weight or more, including all values and subranges therebetween.

In embodiments, the unsaturated phospholipid is present in an amount of at least about 1% by weight, or at least about 2% by weight, or at least about 3% by weight, or at least about 4% by weight, or at least about 5% by weight, or at least about 6% by weight, or at least about 7% by weight, or at least about 8% by weight, or at least about 9% by weight, or at least about 10% by weight, or at least about 11% by weight, or at least about 12% by weight, or at least about 13% by weight, or at least about 14% by weight, or at least about 15% by weight, or at least about 16% by weight, or at least about 17% by weight, or at least about 18% by weight, or at least about 19% by weight, or at least about 20% by weight, or at least about 25% by weight, or at least about 30% by weight, or at least about 35% by weight, or at least about 40% by weight, or at least about 45% by weight, or at least about 50% by weight, or at least about 55% by weight, or at least about 60% by weight, or at least about 65% by weight, or at least about 70% by weight, or at least about 75% by weight, or at least about 80% by weight, or at least about 85% by weight, or at least about 90% by weight, or more of the liposomal carrier.

In embodiments, cholesterol, and phospholipid content in liposomal carriers of the present disclosure is determined by HPLC/UV.

Phosphatidylcholines, including those obtained from natural sources or partially or fully synthetic are suitable for use in the liposomal carriers of the present disclosure.

Non-limiting examples of phospholipids suitable for use in the liposomal carriers of the present disclosure include one or more of: 1,2-divaccenoyl-sn-glycero-3-phosphocholine (18:1(11-cis) PC); 1,2-di[(8Z) octadecenoyl]-sn-glycero-3-phosphocholine (18:1 (8-cis) PC); 1,2-dimyristoleoyl-sn-glycero-3-phosphocholine (14:1 (Δ9-Cis) PC); 1,2-dimyristelaidoyl-sn-glycero-3-phosphocholine (14:1 (Δ9-Trans) PC); 1,2-dipalmitoleoyl-sn-glycero-3- phosphocholine (16:1 (Δ9-Cis) PC); 1,2-dipalmitelaidoyl-sn-glycero-3-phosphocholine (16:1 (Δ9-Trans) PC); 1,2-dipetroselenoyl-sn-glycero-3-phosphocholine (18:1 (Δ6-Cis) PC); 1,2-dioleoyl-sn-glycero-3-phosphocholine (18:1 (Δ9-Cis) PC; (DOPC)); 1,2-dielaidoyl-sn-glycero-3-phosphocholine (18:1 (Δ9-Trans) PC); 1,2-dilinoleoyl-sn-glycero-3-phosphocholine (18:2 (Cis) PC (DLPC)); 1,2-dilinolenoyl-sn-glycero-3-phosphocholine (18:3 (Cis) PC); 1,2-dieicosenoyl-sn-glycero-3-phosphocholine (20:1 (Cis) PC); 1,2-diarachidonoyl-sn-glycero-3-phosphocholine (20:4 (Cis) PC); 1,2-dierucoyl-sn-glycero-3-phosphocholine (22:1 (Cis) PC); 1,2-dinervonoyl-sn-glycero-3-phosphocholine (24:1 (Cis) PC); 1,2-didocosahexaenoyl-sn-glycero-3-phosphocholine (22:6 (Cis) PC); 1-pentadecanoyl-2-oleoyl-sn-glycero-3-phosphocholine (15:0-18:1 PC); 1-palmitoyl-2-oleoyl-glycero-3-phosphocholine (16:0-18:1 PC; (POPC)); 1-palmitoyl-2-linoleoyl-sn-glycero-3-phosphocholine (16:0-18:2 PC); 1-palmitoyl-2-arachidonoyl-sn-glycero-3-phosphocholine (16:0-20:4 PC); 1-palmitoyl-2-docosahexaenoyl-sn-glycero-3-phosphocholine (16:0-22:6 PC); 1-stearoyl-2-oleoyl-sn-glycero-3-phosphocholine (18:0-18:1 PC); 1-stearoyl-2-linoleoyl-sn-glycero-3-phosphocholine (18:0-18:2 PC); 1-stearoyl-2-arachidonoyl-sn-glycero-3-phosphocholine (18:0-20:4 PC); 1-stearoyl-2-docosahexaenoyl-sn-glycero-3-phosphocholine (18:0-22:6 PC); 1-oleoyl-2-myristoyl-sn-glycero-3-phosphocholine (18:1-14:0 PC); 1-oleoyl-2-palmitoyl-sn-glycero-3-phosphocholine (18:1-16:0 PC); 1-oleoyl-2-stearoyl-sn-glycero-3-phosphocholine (18:1-18:0 PC); or 1-(8Z-octadecenoyl)-2-palmitoyl-sn-glycero-3-phosphocholine (18:1(n10)-16:0 PC).

In embodiments, the unsaturated phospholipid is POPC or DOPC.

In embodiments, the unsaturated phospholipid is POPC.

In embodiments, at least about 50% of the phospholipids of the liposomal carriers of the present disclosure comprise an unsaturated fatty acid tail at the sn-1 and/or sn-2 position. In embodiments, about 60% of the phospholipids of the liposomal carriers of the present disclosure comprise an unsaturated fatty acid tail at the sn-1 and/or sn-2 position. In embodiments, at least about 70% of the phospholipids of the liposomal carriers of the present disclosure comprise an unsaturated fatty acid tail at the sn-1 and/or sn-2 position. In embodiments, at least about 80% of the phospholipids of the liposomal carriers of the present disclosure comprise an unsaturated fatty acid tail at the sn-1 and/or sn-2 position. In embodiments, at least about 85% of the phospholipids of the liposomal carriers of the present disclosure comprise an unsaturated fatty acid tail at the sn-1 and/or sn-2 position. In embodiments, at least about 90% of the phospholipids of the liposomal carriers of the present disclosure comprise an unsaturated fatty acid tail at the sn-1 and/or sn-2 position. In embodiments, at least about 95%, or at least about 96%, or at least about 97%, or at least about 98%, or at least about 99% or more of the phospholipids of the liposomal carriers of the present disclosure comprise an unsaturated fatty acid tail at the sn-1 and/or sn-2 position. In embodiments, the phospholipids of the liposomal carriers of the present disclosure consist essentially of phospholipids comprising an unsaturated fatty acid tail at the sn-1 and/or sn-2 position. In embodiments, the phospholipids of the liposomal carriers of the present disclosure consist of phospholipids comprising an unsaturated fatty acid tail at the sn-1 and/or sn-2 position.

In embodiments, the the liposomal carriers of the present disclosure of the present disclosure comprise minor amounts of saturated fatty acids (e.g., DPPC). In embodiments, the percentage of phospholipids comprising saturated fatty acid tails at the sn-1 and sn-2 position is at most about 20%, or at most about 15%, or at most about 10%, or at most about 5%, or at most about 4%, or at most about 3%, or at most about 2%, or at most about 1% (of the total amount of phospholipids in the liposomal carrier). In embodiments, the liposomal carriers of the present disclosure are free of phospholipids comprising saturated fatty acid tails at the sn-1 and sn-2 position.

In embodiments, the liposomal carrier of the present disclosure has an average size between about 90 nm and about 240 nm, including between about 90 nm, about 100 nm, about 110 nm, about 120 nm, about 130 nm, about 140 nm, about 150 nm, about 160 nm, about 170 nm, about 180 nm, about 190 nm, about 200 nm, about 210 nm, about 220 nm, about 230 nm, and about 240 nm, including all values and subranges therebetween. In embodiments, the average size of the liposomal carrier is determined by DLS.

In embodiments, the liposomal carriers of the present disclosure of the present disclosure comprises less than about 10% cholesterol by weight, or less than about 9% cholesterol by weight, or less than about 8% cholesterol by weight, or less than about 7% cholesterol by weight, or less than about 6% cholesterol by weight, or less than about 5% cholesterol by weight, or less than about 4% cholesterol by weight, or less than about 3% cholesterol by weight, or less than about 2% cholesterol by weight, or less than about 1% cholesterol by weight, or less than about 0.9% cholesterol by weight, or less than about 0.8% cholesterol by weight, or less than about 0.7% cholesterol by weight, or less than about 0.6% cholesterol by weight, or less than about 0.5% cholesterol by weight, or less than about 0.4% cholesterol by weight, or less than about 0.3% cholesterol by weight, or less than about 0.2% cholesterol by weight, or less than about 0.1% by weight, or less than about 0.5% by weight, or less than about 0.25% by weight, or less than about 0.1% by weight.

In embodiments, the liposomal carriers of the present disclosure comprise less than about 5 mg/mL cholesterol, or less than about 4 mg/mL cholesterol, or less than about 3 mg/ml cholesterol, or less than about 2 mg/mL cholesterol, or less than about 1 mg/mL cholesterol. In embodiments, the cholesterol content is measured by HPLC.

In embodiments, the liposomal carrier of the present disclosure comprises cholesterol in an amount of about 0.01% to about 10% by weight, including from about 0.01% by weight, about 0.025% by weight, about 0.05% by weight, about 0.075% by weight, about 0.1% by weight, about 0.2% by weight, about 0.3% by weight, about 0.4% by weight, about 0.5% by weight, about 0.6% by weight, about 0.7% by weight, about 0.8% by weight, about 0.9% by weight, about 1.0% by weight, about 1.1% by weight, about 1.2% by weight, about 1.3% by weight, about 1.4% by weight, about 1.5% by weight, about 2% by weight, about 3% by weight, about 4% by weight, about 5% by weight, about 6% by weight, about 7% by weight, about 8% by weight, about 9% by weight, to about 10% by weight, including all values and sub-ranges therebetween.

In embodiments, the liposomal carrier comprises cholesterol:phospholipid in a ratio of about 1:10 to 1:100, including about 1:10, about 1:15, about 1:20, about 1:30, about 1:40, about 1:50, about 1:60, about 1:70, about 1:80, about 1:90, about 1:100, including all values and subranges therebetween. In embodiments, the liposomal carrier comprises cholesterol:phospholipid in a ratio of about 1:30 to 1:50. In aspects, the amount of cholesterol in the liposome carrier is up to 1 mg/ml, up to 3 mg/ml, up to 5 mg/ml, up to 7 mg/ml, up to 9 mg/ml, or up to 10 mg/ml. Typically, the amount is below 12 mg/ml. In embodiments, the liposomal carrier, or ophthalmic composition of the present disclosure is free of added cholesterol.

In embodiments, the steroid suitable for use in the ophthalmic compositions of the present disclosure is a corticosteroid.

In embodiments, the steroid is prednisolone, or a prodrug thereof, or derivative thereof. Advantageously for encapsulation in the disclosed embodiments, prednisolone is poorly soluble in water. In aspects, water soluble prednisone variants may be used (e.g., methylprednisolone disodium phosphate, methylprednisolone sodium succinate, prednisolone sodium phosphate, prednisolone sodium succinate, prednisolone acetate).

In embodiments, the steroid has an aqueous solubility of less than about 0.5 mg/mL, or less than about 0.4 mg/mL, or less than about 0.3 mg/mL, or less than about 0.2 mg/mL, or less than about 0.1 mg/mL.

In embodiments, the steroid suitable for use in the ophthalmic compositions of the present disclosure is prednisolone.

In embodiments, about 50% or more of the total steroid content in the composition is encapsulated in the liposomal carrier, or about 60% or more of the total steroid content in the composition is encapsulated in the liposomal carrier, or about 70% or more of the total steroid content in the composition is encapsulated in the liposomal carrier, or about 80% or more of the total steroid content in the composition is encapsulated in the liposomal carrier, or about 85% or more of the total steroid content in the composition is encapsulated in the liposomal carrier, or about 90% or more of the total steroid content in the composition is encapsulated in the liposomal carrier, or about 95% or more of the total steroid content in the composition is encapsulated in the liposomal carrier. In embodiments, about 96%, about 97%, about 98%, about 99% or more of the total steroid content in the composition is encapsulated in the liposomal carrier. In embodiments, about 85-100%, or about 90-100% of the total steroid content in the composition is encapsulated in the liposomal carrier. In embodiments, the encapsulated steroid content is determined by HPLC.

In embodiments, the ophthalmic composition comprises free steroid (e.g., free prednisolone) in less than about 50% of the total steroid content, or less than about 40% of the total steroid content, or less than about 30% of the total steroid content, or less than about 20% of the total steroid content of the total steroid content, or less than about 15% of the total steroid content, or less than about 10% of the total steroid content, or less than about 5% of the total steroid content. In embodiments, the ophthalmic composition comprises free steroid (e.g., free prednisolone) in less than about 15% of the total steroid content. In embodiments, the ophthalmic composition comprises free steroid (e.g., free prednisolone) in less than about 10% of the total steroid content. In embodiments, the free steroid content is determined by HPLC.

In embodiments, the loading of the steroid (e.g., prednisolone) is about 0.1% w/w to about 10% w/w of the liposomal carrier, including from about 0.1% w/w, about 0.5% w/w, about 1.0% w/w, about 1.5% w/w, about 2.0% w/w, about 2.5% w/w, about 3.0% w/w, about 3.5% w/w, about 4.0% w/w, about 4.5% w/w, about 5.0% w/w, about 5.5% w/w, about 6.0% w/w, about 6.5% w/w, about 7.0% w/w, about 7.5% w/w, about 8.0% w/w, about 8.5% w/w, about 9.0% w/w, about 9.5% w/w, to about 10.0% w/w of the liposomal carrier, including all values and subranges therebetween. In embodiments the loading of prednisolone is about 3% w/w to about 10% w/w, about 3% w/w to about 7% w/w, about 3% w/w to about 6% w/w, or about 3% w/w to about 5% w/w of the liposomal carrier.

In embodiments, the loading of the steroid (e.g., prednisolone) is at least about 0.1% w/w, or at least about 0.2% w/w, or at least about 0.3% w/w, or at least about 0.4% w/w, or at least about 0.5% w/w, or at least about 0.6% w/w, or at least about 0.7% w/w, or at least about 0.8% w/w, or at least about 0.9% w/w, or at least about 1.0% w/w, or at least about 1.1% w/w, or at least about 1.2% w/w, or at least about 1.3% w/w, or at least about 1.4% w/w, or at least about 1.5% w/w, or at least about 1.6% w/w, or at least about 1.7% w/w, or at least about 1.8% w/w, or at least about 1.9% w/w, or at least about 2.0% w/w, or at least about 2.1% w/w, or at least about 2.2% w/w, or at least about 2.3% w/w, or at least about 2.4% w/w, or at least about 2.5% w/w, or at least about 2.6% w/w, or at least about 2.7% w/w, or at least about 2.8% w/w, or at least about 2.9% w/w, or at least about 3.0% w/w, or at least about 3.1% w/w, or at least about 3.2% w/w, or at least about 3.3% w/w, or at least about 3.4% w/w, or at least about 3.5% w/w, or at least about 3.6% w/w, or at least about 3.7% w/w, or at least about 3.8% w/w, or at least about 3.9% w/w, or at least about 4.0% w/w, or at least about 4.1% w/w, or at least about 4.2% w/w, or at least about 4.3% w/w, or at least about 4.4% w/w, or at least about, or 4.5% w/w, or at least about 4.6% w/w, or at least about 4.7% w/w, or at least about 4.8% w/w, or at least about 4.9% w/w, or at least about 5.0% w/w of the liposomal carrier. In aspects, the range may be about 2% to about 5%.

In embodiments, the ratio of steroid (e.g., prednisolone): the unsaturated phospholipid is at least about 0.005:1 w/w, or at least about 0.01:1 w/w, or at least about 0.02:1 w/w, or at least about 0.03:1 w/w, or at least about 0.04:1 w/w, or at least about 0.05:1 w/w, or at least about 0.06:1 w/w, or at least about 0.07:1 w/w, or at least about 0.08:1 w/w, or at least about 0.09:1 w/w, or at least about 0.1:1 w/w. In embodiments, the ratio of prednisolone: the unsaturated phospholipids is at least about 0.04:1 w/w.

In embodiments, the ratio of steroid (e.g., prednisolone): the unsaturated phospholipid is about 0.005:1 w/w to about 0.1:1 w/w, including about 0.005:1, about 0.01:1 w/w, about 0.02:1 w/w, about 0.03:1 w/w, about 0.04:1 w/w, about 0.05:1 w/w, about 0.06:1 w/w, about 0.07:1 w/w, about 0.08:1 w/w, about 0.09:1 w/w, to about 0.1:1 w/w, including all values and subranges therebetween. In embodiments, the ratio of prednisolone: the unsaturated phospholipids is about 0.04:1 w/w.

In embodiments, the liposomal carriers, or ophthalmic compositions of the present disclosure comprise from about 0.5-7 mg/mL of the steroid (e.g., prednisolone), including from about 0.5 mg/mL, about 0.6 mg/mL, about 0.7 mg/mL, about 0.8 mg/mL, about 0.9 mg/mL, about 1 mg/mL, about 1.1 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, about 1.9 mg/mL, about 2 mg/mL, about 2.1 mg/mL, about 2.2 mg/mL, about 2.3 mg/mL, about 2.4 mg/mL, about 2.5 mg/mL, about 2.6 mg/mL, about 2.7 mg/mL, about 2.8 mg/mL, about 2.9 mg/mL, about 3 mg/mL, about 3.1 mg/mL, about 3.2 mg/mL, about 3.3 mg/mL, about 3.4 mg/mL, about 3.5 mg/mL, about 3.6 mg/mL, about 3.7 mg/mL, about 3.8 mg/mL, about 3.9 mg/mL, about 4 mg/mL, about 4.1 mg/mL, about 4.2 mg/mL, about 4.3 mg/mL, about 4.4 mg/mL, about 4.5 mg/mL, about 4.6 mg/mL, about 4.7 mg/mL, about 4.8 mg/mL, about 4.9 mg/mL, about 5 mg/mL, about 5.1 mg/mL, about 5.2 mg/mL, about 5.3 mg/mL, about 5.4 mg/mL, about 5.5 mg/mL, about 5.6 mg/mL, about 5.7 mg/mL, about 5.8 mg/mL, about 5.9 mg/mL, about 6 mg/mL, about 6.1 mg/mL, about 6.2 mg/mL, about 6.3 mg/mL, about 6.4 mg/mL, about 6.5 mg/mL, about 6.6 mg/mL, about 6.7 mg/mL, about 6.8 mg/mL, about 6.9 mg/mL, to about 7 mg/mL, including all values and subranges therebetween. In embodiments, the ophthalmic compositions of the present disclosure comprise from about 2-7 mg/mL, or about 3-6 mg/mL, or about 4-6 mg/mL of the steroid (e.g., prednisolone). In embodiments, the steroid content is measured by HPLC.

In embodiments, the liposomal carriers, or ophthalmic compositions of the present disclosure comprise at least about 0.5 mg/mL of the steroid (e.g., prednisolone), or at least about 0.6 mg/mL of the steroid (e.g., prednisolone), or at least about 0.7 mg/mL of the steroid (e.g., prednisolone), or at least about 0.8 mg/mL of the steroid (e.g., prednisolone), or at least about 0.9 mg/mL of the steroid (e.g., prednisolone), or at least about 1 mg/mL of the steroid (e.g., prednisolone), or at least about 1.1 mg/mL of the steroid (e.g., prednisolone), or at least about 1.2 mg/mL of the steroid (e.g., prednisolone), or at least about 1.3 mg/mL of the steroid (e.g., prednisolone), or at least about 1.4 mg/mL of the steroid (e.g., prednisolone), or at least about 1.5 mg/mL of the steroid (e.g., prednisolone), or at least about 1.6 mg/mL of the steroid (e.g., prednisolone), or at least about 1.7 mg/mL of the steroid (e.g., prednisolone), or at least about 1.8 mg/mL of the steroid (e.g., prednisolone), or at least about 1.9 mg/mL of the steroid (e.g., prednisolone), or at least about 2 mg/mL of the steroid (e.g., prednisolone), or at least about 2.1 mg/mL of the steroid (e.g., prednisolone), or at least about 2.2 mg/mL of the steroid (e.g., prednisolone), or at least about 2.3 mg/mL of the steroid (e.g., prednisolone), or at least about 2.4 mg/mL of the steroid (e.g., prednisolone), or at least about 2.5 mg/mL of the steroid (e.g., prednisolone), or at least about 2.6 mg/mL of the steroid (e.g., prednisolone), or at least about 2.7 mg/mL of the steroid (e.g., prednisolone), or at least about 2.8 mg/mL of the steroid (e.g., prednisolone), or at least about 2.9 mg/mL of the steroid (e.g., prednisolone), or at least about 3 mg/mL of the steroid (e.g., prednisolone), or at least about 3.1 mg/mL of the steroid (e.g., prednisolone), or at least about 3.2 mg/mL of the steroid (e.g., prednisolone), or at least about 3.3 mg/mL of the steroid (e.g., prednisolone), or at least about 3.4 mg/mL of the steroid (e.g., prednisolone), or at least about 3.5 mg/mL of the steroid (e.g., prednisolone), or at least about 3.6 mg/mL of the steroid (e.g., prednisolone), or at least about 3.7 mg/mL of the steroid (e.g., prednisolone), or at least about 3.8 mg/mL of the steroid (e.g., prednisolone), or at least about 3.9 mg/mL of the steroid (e.g., prednisolone), or at least about 4 mg/ml of the steroid (e.g., prednisolone), or at least about 4.1 mg/mL of the steroid (e.g., prednisolone), or at least about 4.2 mg/mL of the steroid (e.g., prednisolone), or at least about 4.3 mg/mL of the steroid (e.g., prednisolone), or at least about 4.4 mg/mL of the steroid (e.g., prednisolone), or at least about 4.5 mg/mL of the steroid (e.g., prednisolone), or at least about 4.6 mg/mL of the steroid (e.g., prednisolone), or at least about 4.7 mg/mL of the steroid (e.g., prednisolone), or at least or at least about 4.8 mg/mL of the steroid (e.g., prednisolone), or at least about 4.9 mg/mL of the steroid (e.g., prednisolone), or at least about 5 mg/mL of the steroid (e.g., prednisolone), or at least about 5.1 mg/mL of the steroid (e.g., prednisolone), or at least about 5.2 mg/mL of the steroid (e.g., prednisolone), or at least about 5.3 mg/mL of the steroid (e.g., prednisolone), or at least about 5.4 mg/mL of the steroid (e.g., prednisolone), or at least about 5.5 mg/mL of the steroid (e.g., prednisolone), or at least about 5.6 mg/mL of the steroid (e.g., prednisolone), or at least about 5.7 mg/mL of the steroid (e.g., prednisolone), or at least about 5.8 mg/mL of the steroid (e.g., prednisolone), or at least about 5.9 mg/mL of the steroid (e.g., prednisolone), or at least about 6 mg/mL of the steroid (e.g., prednisolone), or at least about 6.1 mg/ml of the steroid (e.g., prednisolone), or at least about 6.2 mg/mL of the steroid (e.g., prednisolone), or at least about 6.3 mg/mL of the steroid (e.g., prednisolone), or at least about 6.4 mg/mL of the steroid (e.g., prednisolone), or at least about 6.5 mg/mL of the steroid (e.g., prednisolone), or at least about 6.6 mg/mL of the steroid (e.g., prednisolone), or at least about 6.7 mg/mL of the steroid (e.g., prednisolone), or at least about 6.8 mg/mL of the steroid (e.g., prednisolone), or at least about 6.9 mg/mL of the steroid (e.g., prednisolone), or at least about 7 mg/mL of the steroid (e.g., prednisolone), including all values and subranges therebetween. In embodiments, the steroid content is measured by HPLC.

In embodiments, the liposomal carrier of the present disclosure is free of polyethylene glycol (PEG) ylated lipid.

In embodiments, the ophthalmic compositions of the present disclosure contain no added PEGylated lipid.

In embodiments, PEGylated lipids are composed of a PEG polymer with a molecular mass between 200 and 20 000 Dalton on the one end and a lipophilic anchoring molecule on the other end. Typically anchoring molecules are chosen from the group of phospholipids and sterols. In embodiments, the PEGylated lipids are PEG 2000-distearoyl phosphatidyl ethanolamine and/or PEG 2000-cholesterol.

In embodiments, the ophthalmic compositions of the present disclosure are free of a mucoadhesive agent.

In embodiments, the ophthalmic compositions of the present disclosure comprise a pharmaceutically acceptable buffering agent. In embodiments, the ophthalmic compositions of the present disclosure comprise phosphate buffered saline (PBS) as a buffer.

In embodiments, the ophthalmic compositions of the present disclosure comprise water.

In embodiments, the pH of ophthalmic compositions of the present disclosure is between about 5 to about 8, including from about 6, about 6.5, about 7, about 7.5, about 8, to about 8.5, including all values and subranges therebetween. In embodiments, the pH of ophthalmic compositions of the present disclosure are between about 5 to about 7, optionally 6 to about 7.5.

In embodiments, the ophthalmic compositions of the present disclosure exhibit an in vitro release profile wherein about 90% or less, about 85% or less, about 80% or less, about 75% or less, about 70% or less, about 65% or less, about 60% or less, about 55% or less, about 50% or less, or about 45% or less, or about 40% or less, or about 35% or less, or about 30% or less, or about 25% or less, or about 20% or less, or about 15% or less, or about 10% or less, or about 5% or less, of steroid (e.g., prednisolone) is released after about 12 hours. In embodiments, the ophthalmic compositions of the present disclosure exhibit an in vitro release profile wherein about 90% or less, about 85% or less, about 80% or less, about 75% or less, about 70% or less, about 65% or less, or about 60% or less, or about 55% or less, or about 50% or less, or about 45% or less, or about 40% or less, or about 35% or less, or about 30% or less, or about 25% or less, or about 20% or less, or about 15% or less, or about 10% or less, or about 5% or less, of steroid (e.g., prednisolone) is released after about 24 hours.

In embodiments, the ophthalmic compositions of the present disclosure exhibit an in vitro release profile wherein about 50% or less of steroid (e.g., prednisolone) is released after about 12 hours and about 65% or less of steroid (e.g., prednisolone) is released after about 24 hours. In embodiments, the in vitro release profile is determined by HPLC.

In embodiments of the ophthalmic compositions of the present disclosure, the leakage of prednisolone from the liposomal carrier is less than about 1%, or less than about 2%, or less than about 3%, or less than about 4%, or less than about 5%, or less than about 6%, or less than about 7%, or less than about 8%, or less than about 9%, or less than about 10%, or less than about 11%, or less than about 12%, or less than about 13%, or less than about 14%, or less than about 15%, or less than about 20%, or less than about 25%, or less than about 30%, or less than about 35%, or less than about 40%, or less than about 45%, or less than about 50%, when stored over 3 weeks at 5° C.

In embodiments, the composition of the present disclosure is a pharmaceutical formulation for injection. In embodiments, the injection is intraocular. In embodiments, the injection is intravitreal or subconjunctival. In embodiments, the injection is intravitreal. In embodiments, the injection is subconjunctival. The injection may be sub-tenon, peribulbar, intracameral or suprachoroidal.

In embodiments, the ophthalmic compositions of the present disclosure are administered (e.g., by injection) so as to deliver about 0.05 mg to about 0.4 mg of the steroid, including about 0.05 mg, about 0.06 mg, about 0.07 mg, about 0.08 mg, about 0.09 mg, about 0.1 mg, about 0.2 mg, about 0.3 mg, or about 0.4 mg, including all values and subranges therebetween. In embodiments, the ophthalmic compositions of the present disclosure are administered so as to deliver about 0.05 mg to about 0.2 mg, or about 0.1 mg to about 0.15 mg, or about 0.1 mg to about 0.125 mg of the steroid.

In embodiments, the ophthalmic compositions of the present disclosure are administered in an injectable volume of about 0.01 mL to about 0.25 mL, including about 0.01 mL, about 0.02 mL, about 0.03 mL, about 0.04 mL, about 0.05 mL, about 0.06 mL, about 0.07 mL, about 0.08 mL, about 0.09 mL, about 0.1 mL about 0.15 mL, about 0.2 mL or 0.35 L, including all values and subranges therebetween. In embodiments, the ophthalmic compositions of the present disclosure are administered in an injectable volume of about 0.03 mL to about 0.05 mL.

In embodiments, the ophthalmic composition of the present disclosure is administered by injection (e.g., intravitreally) so as to deliver about 0.1 to about 0.125 mg of the steroid e.g., in an injectable volume of about 0.05 mL of a 4-6 mg/mL steroid composition.

Liposome formulations may be prepared with unsaturated phospholipid and prednisolone. An illustrative example is shown in Table 11. Lipid and drug (e.g. prednisolone) may be mixed together in a solvent and then dried to evaporate the solvent. Following evaporation to dryness the resulting film containing the lipid and drug may be resuspended in buffer, typically phosphate buffered saline (PBS). Lipid, drug, and PBS may be stirred with magnetic beads and heated in water bath at 55° C. for 45 minutes, before being passed through a thermobarrel extruder at 55° C. To provide a 100 nm diameter liposome, extrusion may be through a 100 nm membrane for one or more passes (e.g. 1, 2, 3, 4, 5, 6). A 200 nm diameter liposome may be a 200 nm membrane for one or more passes (e.g. 1, 2, 3, 4, 5, 6). Optionally, 100 nm or 200 nm liposomes may subsequently be extruded through an 80 nm membrane for one or more passes (e.g. 1, 2, 3, 4, 5, 6).

During preparation of the liposomes, processing time in the water bath (prior to extrusion) may be: up to 45 minutes, up to 60 minutes, up to 90 minutes, up to 120 minutes, or up to 180 minutes. In aspects, longer processing times may be used.

Therapeutic Use

In embodiments, provided herein are methods of treating inflammation of the eye in a subject in need thereof, comprising administering an ophthalmic composition of the present disclosure.

In embodiments, provided herein are methods of treating an ocular disease or disorder in a subject in need thereof comprising administering a ophthalmic composition of the present disclosure. In embodiments, the ocular disease or disorder is a posterior ocular condition. In embodiments, the posterior ocular disease or disorder is acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic ophthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, or glaucoma. Also disclosed are methods of treating post ocular surgery inflammation.

In embodiments, provided herein are methods of treating central retinal vein occlusion (CRVO), branch retinal vein occlusion (BRVO), choroidal macular edema (CME), diabetic macular edema (DME), diabetic macular retinopathy, uveitis, telangitis, or age related macular degeneration (ARMD).

In embodiments, provided herein are methods of treating diabetic retinopathy in a subject in need thereof, comprising administering a ophthalmic composition of the present disclosure. In embodiments, the diabetic retinopathy is non-proliferative diabetic retinopathy or proliferative diabetic retinopathy.

In embodiments, provided herein are methods of treating diabetic macular edema in a subject in need thereof, comprising administering a ophthalmic composition of the present disclosure.

In embodiments, provided herein are methods of treating retinal vein occlusion (RVO) in a subject in need thereof, comprising administering a ophthalmic composition of the present disclosure. In embodiments, the RVO is branch retinal vein occlusion (BRVO), or central retinal vein occlusion (CRVO).

In embodiments of the methods disclosed herein wherein a disease or condition of the eye is treated, the compositions of the present disclosure can be injected (e.g., into the vitreous or other locations in the posterior segment of the eye, or into the anterior chamber) so as to deliver a dose of steroid as described herein (e.g., a 4-6 mg/mL, or about 5 mg/mL ophthalmic composition, or e.g., about 0.1 to about 0.15 mg of the steroid in an injectable volume of about 0.05 mL).

In embodiments, the methods of the present disclosure comprise injecting into the posterior segment of the eye an ophthalmic composition described herein.

EXAMPLES

Example 1: Preparation and Evaluation of DPPC or POPC Liposome Carriers with Prednisolone Analytical Methods
Particle Size Particle size was assessed by dynamic light scattering (DLS) using an Anton Paar Litesizer 500, by sampling 50 µL of the liposomes and preparing a 1:20 dilution in 0.9% sodium chloride solution (test method TM03-02).
DLS Method: TM03-02

More specifically, the method TM03-02 was used for the determination of mean particle size (the mean particle size may also be referred to herein as average diameter or size with respect to liposomes) and polydispersity index (PDI) for liposomal formulations. An Anton Paar Litesizer 500 instrument and Anton Paar Kalliope software were used to perform the analysis. The instrument was calibrated prior to each experiment (acceptable hydrodynamic diameter=207.76–222.36 nm; acceptable PDI=<10%). An HPLC vial was rinsed with filtered saline and then filled with 1 mL of filtered saline. The vial was then inverted 5 times. To this vial, 50 µL of sample to be tested was added to the 1 mL saline to achieve an approximate lipid concentration of 0.5 mg/mL (or within 0.2-1.0 mg/mL). The vial was inverted 5 times to combine. 1 mL of this solution was then transferred to a cuvette (Anton Paar Cat. No. 164435), capped, wiped with lint-free tissue, inserted into the instrument, and secured with a thermal cap. The following parameters were used: temperature=23° C.; Number of runs=automatic (or selected 20 runs if for batch release); Run duration=10 seconds (or selected 30 seconds if for batch release); Material=phospholipids; Solvent=154 mM NaCl; User-defined D-values=10, 50, 90.
HPLC The HPLC-UV methods developed during these studies are listed in Table 1.

TABLE 1

| Analytical methods | |
|---|---|
| Method | Description |
| DM55 | Determination of Prednisolone Content in Liposomes by HPLC |
| DM59 | Determination of Cholesterol and POPC in Liposomes by HPLC/UV |
| DM60 | Determination of Prednisolone Liposome Drug Release by HPLC |
| DM61 | Determination of Prednisolone and Related Substances in Liposomes by HPLC |
| DM62 | Determination of DPPC in Liposomes by HPLC/UV |

HPLC Method: DM55

The DM55 HPLC method was used to determine prednisolone content in liposome formulations that contain prednisolone as the active pharmaceutical ingredient (API). Briefly, a reverse phase HPLC with UV detection was set to 244 nm (see Table 2).

A standard solution (STD1) was prepared by adding 4.25 mg of prednisolone to a 25 mL volumetric flask, making up the volume with standard diluent (90% methanol, 10% water, 0.05% acetic acid), and sonicating for 3 minutes to dissolve. STD2 was prepared as a duplicate of STD1. The final prednisolone concentration for STD1 and STD2 was 0.17 mg/mL. A liposome sample solution was prepared: 50 µL of sample to be measured was added into a 2 mL glass HPLC vial. To this, 1.45 mL of diluent (Table 2) was added and vortexed 10 seconds to mix. Procedure was scaled as needed. The HPLC system was equilibrated with mobile phased until a stable baseline was obtained. An exemplary analysis sequence is provided below (Table 3).

TABLE 2

| HPLC conditions for the analytical methods | | | | | | |
|---|---|---|---|---|---|---|
| Method | Column | Mobile Phase A | Mobile Phase B | Mobile Phase C | Diluent | Column Temp (° C.) |
| DM55 | Waters X Select ® CSH C18, 3.0 × 150 mm, ID 3.5 µm | 0.05% $H_3PO_4$ in water | 100% Acetonitrile | 100% Methanol | 0.05% Glacial Acetic Acid in methanol | 40 |
| DM59 | Waters X Select ® CSH C18, 3.0 × 150 mm, ID 3.5 µm | 0.05% $H_3PO_4$ in water | 100% Methanol | NA | 0.05% Glacial Acetic Acid in methanol | 45 |
| DM60 | Waters X Select ® CSH C18, 3.0 × 150 mm, ID 3.5 µm | 0.05% $H_3PO_4$ in water | 100% Acetonitrile | 100% Methanol | SSTDL: 0.05% Glacial Acetic Acid in methanol STDL: 0.05% Glacial Acetic Acid in water | 40 |

TABLE 2-continued

HPLC conditions for the analytical methods

| | | | | | | |
|---|---|---|---|---|---|---|
| DM61 | YMC-Pack Pro C18, 150 × 3.0 mm, S-3 μm, 12 nm | 0.05% $H_3PO_4$ in water | 100% Acetonitrile | NA | SPDL: 94% Methanol-6% Water-0.05% Acetic acid STDL: 90% Methanol-10% Water-0.05% Acetic acid | 45 |
| DM62 | Waters X Select ® CSH C18, 3.0 × 150 mm, ID 3.5 μm | 0.05% $H_3PO_4$ in water | 100% Methanol | NA | 0.05% Glacial Acetic Acid in methanol | 45 |
| DM63 | GL Sciences Inertsil ODS-3V 3.0 × 150 mm, ID 5 μm | 25 mM Hexyl-ammonium Acetate (HAA) | 100% Acetonitrile | NA | Water | 40 |

| Method | λ (nm) | Flow Rate (mL/min) | Inj. Vol (μL) | Nominal Conc (mg/mL) | Run Time (min) | Isocratic/Gradient |
|---|---|---|---|---|---|---|
| DM55 | 244 | 0.5 | 5 | 0.25 | 6 | Isocratic: 48% A-26% B-26% C |
| DM59 | 205 | 0.6 | 5 | 0.6 for CHOL 6 for POPC | 12 | Gradient: |

| Time (min) | Flow rate (mL/min) | % A | % B |
|---|---|---|---|
| 0 | 0.6 | 7 | 93 |
| 0.5 | 0.6 | 3 | 97 |
| 7 | 0.6 | 3 | 97 |
| 8 | 0.6 | 7 | 93 |
| 12 | 0.6 | 7 | 93 |

| Method | λ (nm) | Flow Rate (mL/min) | Inj. Vol (μL) | Nominal Conc (mg/mL) | Run Time (min) | Isocratic/Gradient |
|---|---|---|---|---|---|---|
| DM60 | 244 | 0.5 | 10 | 0.025 0.10 | 6 | Isocratic: 48% A-26% B-26% C |
| DM61 | 244 | 0.6 | 8 | 0.17 | 28 | Gradient: |

| Time (min) | Flow rate (mL/min) | % A | % B |
|---|---|---|---|
| 0 | 0.6 | 80 | 20 |
| 13 | 0.6 | 70 | 30 |
| 20 | 0.6 | 35 | 65 |
| 24 | 0.6 | 35 | 65 |
| 24.1 | 0.6 | 80 | 20 |
| 28 | 0.6 | 80 | 20 |

| Method | λ (nm) | Flow Rate (mL/min) | Inj. Vol (μL) | Nominal Conc (mg/mL) | Run Time (min) | Isocratic/Gradient |
|---|---|---|---|---|---|---|
| DM62 | 210 | 0.6 | 20 | 2.1 | 12 | Gradient: |

| Time (min) | Flow rate (mL/min) | % A | % B |
|---|---|---|---|
| 0 | 0.6 | 7 | 93 |
| 0.5 | 0.6 | 3 | 97 |
| 7 | 0.6 | 3 | 97 |
| 8 | 0.6 | 7 | 93 |
| 12 | 0.6 | 7 | 93 |

| Method | λ (nm) | Flow Rate (mL/min) | Inj. Vol (μL) | Nominal Conc (mg/mL) | Run Time (min) | Isocratic/Gradient |
|---|---|---|---|---|---|---|
| DM63 | 244 | 1.0 | 20 | 0.02 | 15 | Gradient: |

| Time (min) | Flow rate (mL/min) | % A | % B |
|---|---|---|---|
| 0 | 1.0 | 78 | 22 |
| 8 | 1.0 | 56 | 44 |
| 9 | 1.0 | 35 | 65 |
| 12 | 1.0 | 30 | 70 |
| 12.1 | 1.0 | 78 | 22 |
| 15 | 1.0 | 78 | 22 |

TABLE 3

Exemplary analysis sequence

| Solution Name | Number of Injections | Purpose |
|---|---|---|
| Diluent | 1 | Blank |
| STD1 | 3 | Calibration & System Suitability |
| STD2 | 2 | Check & Calibration Standard |
| Samples (up to 20 samples) | 1 | Sample analysis |
| STD1 | 2 | Calibration & System Suitability |

Exemplary system suitability requirements are provided in Table 4.

TABLE 4

Exemplary system suitability

| Property | Acceptable Value |
|---|---|
| RSD[a] of peak areas of prednisolone peak from 5 replicate injections of STD1 | NMT[b] 2.0% |
| RSD[a] of retention times of prednisolone peak from 5 replicate injections of STD1 | NMT[b] 2.0% |
| Agreement between response factors of STD1 and STD2 | 98.0-102.0% |
| Average USP[c] tailing factor of prednisolone peak from 5 replicate injections of STD1 | NMT[b] 2.0 |
| Average USP[c] plate count of prednisolone peak from 5 replicate injections of STD1 | NLT[d] 3000 |

[a]RSD: relative standard deviation
[b]NMT: not more than
[c]USP: United States Pharmacopeia
[d]NLT: not less than HPLC settings (e.g., flow rate, run time, etc.) for running DM55 are found in Table 2. The retention time for prednisolone was about 3.1 minutes. The retention time of the principal peak for the sample solution corresponded with the retention time for the principal peak produced by the prednisolone standard solutions (STD1 and STD2), and did not vary by more than 5%.

HPLC Method: DM59

The DM59 HPLC method was used to quantify and identify cholesterol (CHOL) and 1-palmitoyl-2-oleoyl-sn-glycero-3-phosphocholine (POPC) in liposome samples that contained prednisolone as an API and CHOL and POPC as lipids. Briefly, CHOL and POPC in liposomes were determined using reverse phase HPLC at a detection wavelength of 205 nm (see Table 2).

A standard solution (STD1) was prepared by adding 6 mg of CHOL and 60 mg of POPC to a 10 mL volumetric flask, adding 8 mL of diluent (Table 2), and 0.5 mL of water, and then adding diluent to 10 mL. The sample was then sonicated for 3 minutes to dissolve. STD2 was prepared as a duplicate of STD1. Procedure was scaled as needed. The final CHOL and POPC concentrations for STD1/STD2 were 0.6 mg/mL and 6.0 mg/mL, respectively. Standards were stored at −20° C. A liposome sample solution was prepared for the liposome formulation that contained 12 mg/mL CHOL and 120 mg/mL POPC: 50 µL of sample to be measured was added into a 2 mL glass HPLC vial. To this, 0.95 mL of diluent was added and vortexed 20 seconds to mix. Procedure was scaled as needed. The HPLC system was equilibrated with mobile phased until a stable baseline was obtained. An exemplary analysis sequence is provided in Table 3. Exemplary system suitability requirements are provided in Table 5.

TABLE 5

Exemplary system suitability

| Property | Acceptable Value |
|---|---|
| RSD[a] of peak areas for CHOL and POPC from 5 replicate injections of STD1 | NMT[b] 2.0% |
| RSD[a] of retention times for CHOL and POPC from 5 replicate injections of STD1 | NMT[b] 2.0% |
| Recovery of CHOL and POPC in check STD2 | 97.0-103.0% |
| Average USP[c] tailing factor for CHOL and POPC peak from 5 replicate injections of STD1 | NMT[b] 2.0 |
| Average USP[c] plate count for CHOL and POPC peak from 5 replicate injections of STD1 | NLT[d] 5000 |

[a]RSD: relative standard deviation
[b]NMT: not more than
[c]USP: United States Pharmacopeia
[d]NLT: not less than HPLC settings (e.g., flow rate, run time, etc.) for running DM59 are found in Table 2. The retention time CHOL and POPC were about 6.7 minutes and 7.7 minutes, respectively. The retention time of the principal peak for the sample solution corresponded with the retention time for the principal peak produced by the CHOL and POPC working standard, and did not vary by more than 5%.

HPLC Method: DM60

The DM60 HPLC method was used to determine prednisolone content in the receptor phase of prednisolone liposome drug release study. The method is suitable for the determination of prednisolone released through the dialysis of prednisolone liposome samples. Briefly, a reverse phase HPLC with UV detection was set to 244 nm (see Table 2). Unless otherwise specified, prednisolone release was measured herein using the DM60 HPLC method.

A stock standard solution (Stock STD1) was prepared by adding 6.25 mg of prednisolone to a 25 mL volumetric flask, adding 20 mL of STD diluent (SSTDL; 0.05% acetic acid in methanol), 1.25 mL of water, then adding SSTDL to 25 mL, and sonicating for 3 minutes to dissolve. Stock STD2 was prepared as a duplicate of Stock STD1. The final prednisolone concentration for Stock STD1 and Stock STD2 was 0.25 mg/mL.

A working standard solution (STD1) was prepared according to Table 6.

TABLE 6

Exemplary working standard solutions

| Solution Name | Aliquot (mL) | Stock Solution | Final Volume with STD Diluent (mL) | Concentration (mg/mL) |
|---|---|---|---|---|
| STD1 | 1 | Stock STD1 | 10 | 0.025 |
| STD2 | 4 | Stock STD2 | 10 | 0.10 |

A sample solution of prednisolone, released into buffer solution through dialysis, was used as-is and injected neat for analysis.

The HPLC system was equilibrated with mobile phased until a stable baseline was obtained. An exemplary analysis sequence is provided below (Table 7).

TABLE 7

Exemplary analysis sequence

| Solution Name | Number of Injections | Purpose |
|---|---|---|
| Diluent | 1 | Blank |
| STD1 | 3 | Calibration & System Suitability |
| STD2 | 2 | Check & Calibration Standard |
| Samples (up to 20 samples) | 2 | Sample analysis |
| STD1 | 2 | Calibration & System Suitability |

Exemplary system suitability requirements are provided in Table 8.

TABLE 8

Exemplary system suitability

| Property | Acceptable Value |
|---|---|
| $RSD^a$ of peak areas of prednisolone from 5 replicate injections of STD1 | $NMT^b$ 2.0% |
| $RSD^a$ of retention times of prednisolone peak from 5 replicate injections of STD1 | $NMT^b$ 2.0% |
| Agreement between the response factors of STD1 and STD2 | 97.0-103.0% |
| Average $USP^c$ tailing factor of prednisolone peak from 5 replicate injections of STD1 | $NMT^b$ 2.0 |
| Average $USP^c$ plate count of prednisolone peak from 5 replicate injections of STD1 | $NLT^d$ 3000 |

$^a$RSD: relative standard deviation
$^b$NMT: not more than
$^c$USP: United States Pharmacopeia
$^d$NLT: not less than HPLC settings (e.g., flow rate, run time, etc.) for running DM60 are found in Table 2. The retention time for prednisolone was about 3.2 minutes. The retention time of the principal peak for the sample solution corresponded with the retention time for the principal peak produced by the prednisolone standard solution (STD1 and STD2), and did not vary by more than 5%.

HPLC Method: DM61

The DM61 HPLC method was used to determine prednisolone content in liposome formulations that contain prednisolone as the API. The method is suitable for determination of prednisolone content and related substances in liposome samples. Briefly, a reverse phase HPLC with UV detection was set to 244 nm (see Table 2); Chromatograph data system: Waters Empower 3. A standard solution (STD1) was prepared by adding 4.25 mg of prednisolone to a 25 mL volumetric flask, making up the volume with standard diluent (90% methanol, 10% water, 0.05% acetic acid), and sonicating for 3 minutes to dissolve. STD2 was prepared as a duplicate of STD1. The final prednisolone concentration for STD1 and STD2 was 0.17 mg/mL. A liposome sample solution was prepared: 50 µL of sample to be measured was added into a 2 mL glass HPLC vial. To this, 1.45 mL of SPDL (Table 2) was added and vortexed 10 seconds to mix. Procedure was scaled as needed. The HPLC system was equilibrated with mobile phased until a stable baseline was obtained. An exemplary analysis sequence is provided in Table 7. Exemplary system suitability requirements are provided in Table 9.

TABLE 9

Exemplary system suitability

| Property | Acceptable Value |
|---|---|
| $RSD^a$ of peak areas of prednisolone peak from 5 replicate injections of STD1 | $NMT^b$ 2.0% |
| $RSD^a$ of retention times of prednisolone peak from 5 replicate injections of STD1 | $NMT^b$ 2.0% |
| Agreement between response factors of STD1 and STD2 | 98.0-102.0% |
| Average $USP^c$ tailing factor of prednisolone peak from 5 replicate injections of STD1 | $NMT^b$ 2.0 |
| Average $USP^c$ plate count of prednisolone peak from 5 replicate injections of STD1 | $NLT^d$ 5000 |

$^a$RSD: relative standard deviation
$^b$NMT: not more than
$^c$USP: United States Pharmacopeia
$^d$NLT: not less than HPLC settings (e.g., flow rate, run time, etc.) for running DM61 are found in Table 2. The retention time for prednisolone was about 13 minutes. The retention time of the principal peak for the sample solution corresponded with the retention time for the principal peak produced by the prednisolone standard solution (STD1 and STD2), and did not vary by more than 5%.

HPLC Method: DM62

The DM62 HPLC method was used to quantify and identify dipalmitoylphosphatidylcholine (DPPC) in liposome samples than contained prednisolone as the API and DPPC as lipids. Briefly, a reverse phase HPLC with UV detection was set to 210 nm (see Table 2).

A standard solution (STD1) was prepared by adding 21 mg of DPPC to a 10 mL volumetric flask, adding 8 mL of diluent (0.05% acetic acid in methanol) and 0.25 mL of water, then adding diluent to 10 mL, and sonicating for 3 minutes to dissolve. STD2 was prepared as a duplicate of STD1. The final DPPC concentration for STD1 and STD2 was 0.21 mg/mL. Procedure was scaled as needed. Standard solutions were stored at −20° C.

A liposome sample solution was prepared: 40 µL of liposome sample to be measured was added into a 2 mL glass HPLC vial. To this, 1.50 mL of diluent (Table 2) was added and vortexed 20 seconds to mix. Procedure was scaled as needed. The HPLC system was equilibrated with mobile phased until a stable baseline was obtained. An exemplary analysis sequence is provided in Table 3. Exemplary system suitability requirements are provided in Table 10.

TABLE 10

Exemplary system suitability

| Property | Acceptable Value |
|---|---|
| $RSD^a$ of peak areas of DPPC from 5 replicate injections of STD1 | $NMT^b$ 2.0% |
| $RSD^a$ of retention times for DPPC from 5 replicate injections of STD1 | $NMT^b$ 2.0% |
| The recovery of DPPC in check STD2 | 97.0-103.0% |
| Average $USP^c$ tailing factor for DPPC peak from 5 replicate injections of STD1 | $NMT^b$ 2.0 |
| Average $USP^c$ plate count for DPPC peaks from 5 replicate injections of STD1 | $NLT^d$ 5000 |

$^a$RSD: relative standard deviation
$^b$NMT: not more than
$^c$USP: United States Pharmacopeia
$^d$NLT: not less than HPLC settings (e.g., flow rate, run time, etc.) for running DM62 are found in Table 2. The retention time for DPPC was about 7.0 minutes. The retention time of the principal peak for the sample solution corresponded with the retention time for the principal peak produced by the DPPC standard solution, and did not vary by more than 5%.

Preparation of Liposome Carriers

Liposome formulations were prepared with 50 mg/mL DPPC or POPC, with 5 mg/mL prednisolone. The samples were prepared at 10 mL scale with the composition as shown in Table 11. The lipid, drug, and PBS were stirred with magnetic beads and heated in water bath at 55° C. for 45 minutes, before being passed through a thermobarrel extruder at 55° C. The sample for Formulation 1 was extruded once through a 100 nm membrane, then an 80 nm membrane for a further 6 passes. The sample for Formulation 2 was extruded once through a 200 nm membrane, then an 80 nm membrane for a further 6 passes.

Vesicle size was evaluated after each pass through the 80 nm membrane, following test method TM03-02. The samples were cooled to room temperature, then sampled for HPLC analysis (see HPLC methods: DM55) after 2 hours, and stored at 5° C.

TABLE 11

Composition of DPPC and POPC liposomes with prednisolone

| | Formulation ID: | | | | | |
|---|---|---|---|---|---|---|
| | Formulation 1 | | | Formulation 2 | | |
| Material | % | Target mass (g) | Actual mass (g) | % | Target mass (g) | Actual mass (g) |
| PBS | 94.5 | 9.7 mL | 9.7 mL | 94.5 | 9.7 mL | 9.7 mL |
| POPC | 5 | 0.5 | 0.5027 | 0 | 0 | 0 |
| DPPC | 0 | 0 | 0 | 5 | 0.5 | 0.4987 |
| Prednisolone | 0.5 | 0.05 | 0.0501 | 0.5 | 0.05 | 0.0511 |

Results

Particle size results are presented in Table 12.

TABLE 12

Particle size after each extrusion - POPC and DPPC prednisolone liposomes

| | Formulation 1 | | Formulation 2 | |
|---|---|---|---|---|
| Extrusion pass | Average size (nm) | Polydispersity index (%) | Average size (nm) | Polydispersity index (%) |
| 1 | 821.1 | 24.3 | 887.3 | 29.6 |
| 2 | 174.81 | 19.9 | 136.78 | 20.3 |
| 3 | 125.93 | 22.4 | 114.62 | 9.5 |
| 4 | 118.91 | 13.7 | 2.44 | 24.6 |
| 5 | 114.14 | 1.3 | 127.08 | 26.5 |
| 6 | 101.97 | 14.3 | 109.51 | 12.5 |

Samples were analyzed by HPLC for prednisolone content after extrusion, and again after 24 hours storage at 5° C. Samples were filtered through a 0.2 μm syringe filter before analysis, and compared to unfiltered samples, to remove any precipitated prednisolone and determine the amount that remained dispersed in the liposomes. Appearance and HPLC analytical results are shown in Table 13.

TABLE 13

Analysis of POPC and DPPC prednisolone liposomes

| Sample | Appearance after extrusion | Prednisolone content - unfiltered (mg/mL) | Prednisolone content - filtered (mg/mL) |
|---|---|---|---|
| Formulation 1 immediately after extrusion | White to off-white translucent suspension | 5.97 | 2.21 |
| Formulation 1 after 24 hr | White to off-white translucent suspension, with some visible white precipitate | 2.94 | 2.23 |
| Formulation 2 immediately after extrusion | White to off-white translucent suspension | 3.61 | 0.73 |
| Formulation 2 after 24 hr | White suspension, with more visible white precipitate | 2.55 | 0.73 |

Conclusions

Prednisolone liposomes with average size of 100 nm were prepared with POPC or DPPC. POPC was found to be better than DPPC for solubilizing and dispersing prednisolone in liposomes.

Example 2: Preparation of 100 nm or 200 nm Liposomes with 120 mg/mL POPC Liposomes and 5 mg/mL Prednisolone & Evaluation of the Effect of Cholesterol The formulations were prepared at 20 mL scale with the composition as shown in Table 14.

The lipid, drug, cholesterol, and PBS were stirred with magnetic beads and heated in water bath at 55° C. for 30 minutes, before being passed through a thermobarrel extruder at 55° C. Samples were extruded initially through a 400 nm membrane, then through a 200 nm, and finally (for the 100 nm target size liposomes) part of the batch was further extruded through an 80 nm membrane. The number of extrusion passes for each sub-batch are summarized in Table 15. Vesicle size was monitored after each extrusion pass following test method TM03-02. Liposome size results are shown in Table 15. The samples were cooled to 5° C. then sampled for total and free drug content by HPLC analysis (see HPLC method: DM55). Free drug content was assessed by centrifuging a 0.5 mL sample of the liposomes in an Amicon Ultra 30 kDa spin filter and analyzing the filtrate.

TABLE 14

Composition of 120 mg/mL POPC liposomes with prednisolone and cholesterol

| | Formulation ID: | | | | | |
|---|---|---|---|---|---|---|
| | Formulation 3 | | | Formulation 4 | | |
| Material | % | Target mass (g) | Actual mass (g) | % | Target mass (g) | Actual mass (g) |
| PBS | 88 | 17.6 | 17.63 | 88 | 17.36 | 17.46 |
| POPC | 12 | 2.4 | 2.4192 | 12 | 2.4 | 2.4068 |
| Cholesterol | 0 | 0 | 0 | 1.2 | 0.24 | 0.2341 |
| Prednisolone | 0.5 | 0.05 | 0.1018 | 0.5 | 0.05 | 0.1026 |

Results

TABLE 15

Extrusion conditions and size analysis for prednisolone liposomes with/without cholesterol

| No. | Target Size (nm) | Extrusion pass | 1 | 2 | 3 | 4 | 5 | 6 | 7 | 8 | 9 |
|---|---|---|---|---|---|---|---|---|---|---|---|
| 3-A | 240 | Membrane Size (nm) | 400 | 400 | 400 | 200 | 200 | | | | |
| | | Measured size (nm), and PDI (%) | 834.9, 22.2% | 536.3, 27.0% | 386.0, 29.1% | 219.1, 28.8% | 306.8, 23.0% | | | | |
| 3-B | 100 | Membrane Size (nm) | 400 | 80 | 200 | 80 | 80 | 80 | 80 | | |
| | | Measured size (nm), and PDI (%) | 1715.8, 24.1% | 211.7, 29.2% | 203.3, 28.6% | 129.9, 18.0% | 114.1, 16.8% | 106.4, 17.1% | 102.1, 18.3% | | |
| 4-A | 240 | Membrane Size (nm) | 400 | 400 | 400 | 200 | 200 | 200 | | | |
| | | Measured size (nm), and PDI (%) | 720.0, 21.9% | 541.5, 32.5% | 372.0, 30.5% | 243.7, 23.6% | 226.3, 23.2% | 215.7, 27.1% | | | |
| 4-B- | 100 | Membrane Size (nm) | As above | As above | As above | As above | As above | As above | 80 | 80 | 80 |
| | | Measured size (nm), and PDI (%) | | | | | | | N.T. | N.T. | 117.4, 22.0% |

The results of prednisolone content are summarized in Table 16.

TABLE 16

Total and free prednisolone content in 200 nm or 100 nm POPC liposomes with or without cholesterol

| Sample | Target size (nm) | Size (nm) | Appearance | Prednisolone content (mg/mL) Total | Free |
|---|---|---|---|---|---|
| Formulation 3-A | 240 | 306.8 | White to off-white homogeneous liposomal suspension | 5.124 | 0.349 |
| Formulation 3-B | 100 | 102.1 | White to off-white homogeneous translucent liposomal suspension | 5.080 | 0.304 |
| Formulation 4-A (with cholesterol) | 240 | 215.7 | White to off-white homogeneous liposomal suspension | 5.185 | 0.369 |
| Formulation 4-B (with cholesterol) | 100 | 117.4 | White to off-white homogeneous translucent liposomal suspension | 5.385 | 0.361 |

The 100 nm samples were evaluated after storage for 3 weeks at 5° C. Both samples appeared as translucent liposomal suspensions with a small amount of visible precipitate present. To assess total amount of soluble prednisolone, the samples were filtered through a 0.2 μm syringe filter and analyzed by HPLC (see HPLC method: DM55). Results, shown in Table 17, indicated that the sample without cholesterol maintained a prednisolone content at around the target value of 5 mg/mL, while the concentration had dropped to 3.1 mg/mL in the sample containing cholesterol.

TABLE 17

Prednisolone content in filtered liposome
samples after 3 weeks at 5° C.

| Sample | Prednisolone content after T = 3 weeks at 5° C. (after filtering) (mg/mL) |
|---|---|
| Formulation 3-B (~100 nm liposomes) | 5.057 |
| Formulation 4-B (~100 nm liposomes with cholesterol) | 3.104 |

Conclusions

It was possible to produce liposomes in the target size ranges of 100 nm or 240 nm diameter. Free prednisolone content appeared to represent less than 10% of the total content.

These results indicate the liposomal formulation with cholesterol was less stable, and the addition of cholesterol to the POPC liposomes had a negative impact on prednisolone loading, with a drop in soluble prednisolone content from 5.4 mg/mL to 3.1 mg/mL after short term storage at 5° C. for 3 weeks, compared to the liposomes without cholesterol, which retained a prednisolone content of 5.1 mg/mL over the same time period.

Example 3: Evaluation of 120 mg/mL POPC Liposomes with Prednisolone or Prednisolone 21-Acetate Experiments were conducted to evaluate formulations containing prednisolone or prednisolone 21-Acetate.

The samples were prepared at 10 mL scale with the composition as shown in Table 18. The lipid, drug, and PBS were stirred with magnetic beads and heated in water bath at 55° C. for 30 minutes, before being passed through a thermobarrel extruder at 55° C. Samples were extruded once through a 200 nm membrane, then 6 times through an 80 nm membrane. For Formulation 5, vesicle size was monitored after each pass through the 80 nm membrane, following test method TM03-02. The samples were cooled to 5° C. then sampled for HPLC analysis (see HPLC method: DM55).

TABLE 18

Composition of 120 mg/mL POPC liposomes with
prednisolone or prednisolone 21-acetate

| | Formulation ID: | | | | | |
|---|---|---|---|---|---|---|
| | Formulation 5 | | | Formulation 6 | | |
| Material | % | Target mass (g) | Actual mass (g) | % | Target mass (g) | Actual mass (g) |
| PBS | 88 | 8.8 | 8.8317 | 88 | 8.8 | 8.8139 |
| POPC | 12 | 1.2 | 1.2048 | 12 | 1.2 | 1.218 |
| Prednisolone | 0.5 | 0.05 | 0.0545 | 0 | 0 | 0 |
| Prednisolone 21-Acetate | 0 | 0 | 0 | 0.5 | 0.05 | 0.053 |

Results

Particle size results are presented in Table 19.

TABLE 19

Particle size prednisolone and prednisolone
21-acetate POPC liposomes

| | Formulation 5 | | Formulation 6 | |
|---|---|---|---|---|
| Extrusion pass | Average size (nm) | Polydispersity index (%) | Average size (nm) | Polydispersity index (%) |
| 1 | 256.7 | 26.3 | NT | NT |
| 2 | 131.43 | 17.8 | NT | NT |
| 3 | 111.39 | 17.8 | NT | NT |
| 4 | 108.99 | 18.1 | NT | NT |
| 5 | 107.48 | 12 | NT | NT |
| 6 | 103.06 | 18 | 106.73 | 15.7 |

Samples were analyzed by HPLC for prednisolone or prednisolone 21-acetate content after 24 hours storage at 5° C. An unfiltered sample and a sample filtered through a 0.2 µm syringe filter were analyzed. Appearance and HPLC analytical results are shown in Table 20.

TABLE 20

Prednisolone or prednisolone 21-acetate content in 120 mg/mL POPC liposomes

| Sample | Appearance after storage at 5° C. overnight | Prednisolone content (mg/mL) | | Prednisolone 21-Acetate content (mg/mL) | |
|---|---|---|---|---|---|
| | | Unfiltered | Filtered | Unfiltered | Filtered |
| Formulation 5 | White to off-white homogeneous translucent liposomal suspension | 5.5 | 5.5 | N/A | N/A |
| Formulation 6 | White to off-white homogeneous translucent liposomal suspension | N/A | N/A | 0.7 | 0.7 |

Conclusions 100 nm liposomes with 120 mg/mL POPC were produced. These liposomes were capable of solubilizing at least 5 mg/mL prednisolone, but only up to 0.7 mg/mL prednisolone 21-acetate, establishing that the POPC liposomes provide especially good loading with prednisolone.

Example 4: Determination of Maximal Prednisolone Loading Capacity of 120 mg/mL POPC Liposomes and Evaluation of Liposome Stability 4.1 Evaluation of the 120 mg/mL POPC Liposome Formulation and 10 mg/mL and 15 mg/ml Prednisolone A study was carried out to determine the maximum prednisolone loading capacity of 120 mg/mL POPC liposomes by adding an excess amount of prednisolone, including one sample in which cholesterol was added at 1:10 ratio of the total lipid.

Samples were prepared at 10 mL scale, with an excess amount of prednisolone added, as shown in Table 21. The lipid, drug, cholesterol, and PBS were stirred with magnetic stir bars and heated in a water bath at 60° C. for 60 minutes, before being passed through a thermobarrel extruder at 60° C. The sample used to prepare Formulation 7 was extruded through a 400 nm membrane three times only. The sample used to prepare Formulation 8 was pre-filtered through at 5 µm filter, then extruded through a 400 nm membrane 3 times, and an 80 nm membrane 8 times. The sample used to prepare Formulation 9 was pre-filtered through at 5 µm filter, then extruded through a 400 nm membrane 2 times, and an 80 nm membrane once.

TABLE 21

Composition of 120 mg/mL POPC liposomes with prednisolone and cholesterol

| | Description: | | | | | | | | |
|---|---|---|---|---|---|---|---|---|---|
| | 10 mg/mL Prednisolone | | | 15 mg/mL Prednisolone | | | 10 mg/mL Prednisolone & 12 mg/mL Cholesterol | | |
| | Formulation ID: | | | | | | | | |
| | Formulation 7 | | | Formulation 8 | | | Formulation 9 | | |
| Material | % | Target mass (g) | Actual mass (g) | % | Target mass (g) | Actual mass (g) | % | Target mass (g) | Actual mass (g) |
| PBS | 88 | 8.8 | 8.83 | 88 | 8.8 | 8.9 | 88 | 8.8 | 8.83 |
| POPC | 12 | 1.2 | 1.1935 | 12 | 1.2 | 1.1984 | 10.8 | 1.08 | 1.0735 |
| Cholesterol | 0 | 0 | 0 | 0 | 0 | 0 | 1.2 | 0.12 | 0.1224 |
| Prednisolone | 1 | 0.1 | 0.1048 | 1.5 | 0.15 | 0.1513 | 1 | 0.1 | 0.1065 |

Vesicle size was assessed using test method TM03-02.

The samples were cooled to 5° C. for one hour, then filtered through a 0.45 micron syringe filter, and assayed for prednisolone, POPC, and cholesterol content by HPLC (see HPLC methods: DM55 and DM59). The remainder of the filtered samples were stored at 25° C. for 7 days, then filtered again and assayed for prednisolone content to determine the remaining amount of solubilized drug.

Results are shown in Table 22.

TABLE 22

Vesicle size and Prednisolone content in POPC liposomes with or without cholesterol

| Sample | Size (nm) | Polydispersity index (%) | POPC content (mg/mL) | Cholesterol content (mg/mL) | Prednisolone content (mg/mL) | |
|---|---|---|---|---|---|---|
| | | | | | Initial | 7 days at 25° C. |
| Formulation 7 | 242.5 | 26.6 | 121.7 | ND | 5.071 | 4.958 |
| Formulation 8 | 95.58 | 14.5 | 127.6 | ND | 6.745 | 4.842 |
| Formulation 9 (with cholesterol) | 598.1 | 19.6 | 94.7 | 3.47 | 4.493 | 2.889 |

Conclusions

After adding excess (10 to 15 mg/mL) prednisolone to the 120 mg/mL POPC liposomal formulation, it was found that the initial prednisolone content was as high as 6.7 mg/mL, however, after storage for 7 days, some of the prednisolone was lost due to precipitation, as confirmed by a drop in concentration of prednisolone in the filtered samples. The maximum prednisolone loading capacity in the 120 mg/mL POPC liposome formulation was approximately 5 mg/mL based on these experiments.

Addition of cholesterol, as in the previous experiment, led to a reduction in the prednisolone loading capacity, to approximately 2.9 mg/mL.

4.2 Evaluation of the 120 mg mL POPC Liposome Formulation and 5 mg mL-6.5 mL Prednisolone Fresh samples of liposomes with 5 mg/mL prednisolone, with or without 3 mg/ml cholesterol, were prepared with a target size of 100 nm. Additional samples with higher prednisolone content (5.5 and 6.0 mg/mL), without cholesterol, were prepared to confirm whether >5 mg/mL prednisolone could be achieved.

Sample compositions are outlined in Table 23 and Table 24. Batches were prepared at 12 gram scale, at a temperature of 60° C. The samples were stirred at a temperature of 60° C. for 90 minutes prior to extrusion at 60° C. in a thermo-barrel extruder. Formulations 10 and 12 were extruded 3 times through a 400 nm membrane, then 6 times through an 80 nm membrane. Formulations 11 and 13 were extruded 3 times through a 400 nm membrane, twice through a 200 nm membrane, and 6 times through an 80 nm membrane. The samples were stored at 5° C. after extrusion.

TABLE 23

Composition of 120 mg/mL POPC liposomes with prednisolone and cholesterol

| | Description: | | | | |
|---|---|---|---|---|---|
| | 5 mg/mL Prednisolone | | 5.0 mg/mL Prednisolone & 3.0 mg/mL Cholesterol | | |
| | Formulation ID: | | | | |
| | Formulation 10 | | Formulation 11 | | |
| Material | % | Target mass (g) | Actual mass (g) | % | Target mass (g) | Actual mass (g) |
| PBS | 88.36 | 10.60 | 10.61 | 88.06 | 10.57 | 10.52 |
| POPC | 12 | 1.44 | 1.4521 | 10.8 | 1.44 | 1.4278 |
| Cholesterol | 0 | 0 | 0 | 0.3 | 0.036 | 0.035 |
| Prednisolone | 0.5 | 0.06 | 0.0613 | 0.5 | 0.06 | 0.0601 |

TABLE 24

Composition of 120 mg/mL POPC liposomes with 5.5 mg/mL and 6.0 mg/mL prednisolone

| | | Description: | | | | | |
|---|---|---|---|---|---|---|---|
| | | 5.5 mg/mL Prednisolone | | | 6.0 mg/mL Prednisolone | | |
| | | Formulation ID: | | | | | |
| | | Formulation 12 | | | Formulation 13 | | |
| Material | Raw material ID | % | Target mass (g) | Actual mass (g) | % | Target mass (g) | Actual mass (g) |
| PBS | 6J22 | 88.31 | 10.60 | 10.59 | 88.26 | 10.59 | 10.59 |
| POPC | 22138 | 12 | 1.44 | 1.4346 | 12 | 1.44 | 1.4764 |
| Cholesterol | 22114 | 0 | 0 | 0 | 0 | 0 | 0 |
| Prednisolone | 22368 | 0.55 | 0.066 | 0.0667 | 0.6 | 0.072 | 0.0724 |

Formulations 10-13 were stored at 5° C. for 5 days, then analyzed for prednisolone content, before and after filtering through a 0.2 μm syringe filter. Results are shown in Table 25.

TABLE 25

Prednisolone content in liposome Formulations 10-13

| | | Prednisolone content (mg/mL) | |
|---|---|---|---|
| Sample ID | Description | Before filtering | Filtered |
| Formulation 10 | 5 mg/mL prednisolone liposomes | 5.303 | 5.327 |
| Formulation 11 | 5 mg/mL prednisolone liposomes with 3 mg/mL cholesterol | 5.413 | 5.402 |
| Formulation 12 | 5.5 mg/mL prednisolone liposomes | 5.833 | 5.875 |
| Formulation 13 | 6 mg/mL prednisolone liposomes | 6.441 | 6.284 |

Stability of vesicle size was evaluated by DLS, before and after 0.2 μm filtering (after storing at 5° C. for 5 days), and also after a further storage period of 2 and 8 days. Samples were also assessed after re-filtering at the 8 day timepoint. Results are shown in Table 26.

TABLE 26

Size stability of liposome formula

| | | Average size, nm, and (polydispersity index, %) | | | | |
|---|---|---|---|---|---|---|
| Sample ID | Description | Initial (unfiltered) | Initial (filtered) | T = 2 days | T = 8 days | T = 8 days (refiltered) |
| Formulation 10 | 5 mg/mL prednisolone liposomes | 141.22 (23.4) | 117.83 (23.8) | 117.84 (24.6) | 114.44 (24.3) | 118.14 (25.2) |
| Formulation 11 | 5 mg/mL prednisolone liposomes with 3 mg/mL cholesterol | 91.79 (17.7) | 92.95 (15.9) | 93.76 (9.9) | 94.90 (9.4) | 91.04 (11.0) |
| Formulation 12 | 5.5 mg/mL prednisolone liposomes | 96.53 (22.1) | 97.31 (19.6) | 100.37 (11.7) | N.T. | N.T. |
| Formulation 13 | 6 mg/mL prednisolone liposomes | 96.20 (10.8) | 95.46 (15.2) | 95.05 (9.7) | N.T. | N.T. |

Conclusions

The 120 mg/mL POPC liposome formulation was confirmed as being able to solubilize at least 5 mg/mL prednisolone, and possibly up to 6.5 mg/mL, based on the short term stability evaluation of drug content when stored at 5° C. This was higher than previous experiments and may have been due to the increased temperature of 60° C. and longer processing time before extrusion.

The addition of a lower amount (3 mg/mL) of cholesterol resulted in stable loading of 5 mg/mL prednisolone, unlike in previous formulations. These data show that lower dose cholesterol is compatible with POPC liposome carrier formulations.

Stability of Prednisolone Liposomes after storing for 3 Weeks

A second batch of prednisolone liposomes, without cholesterol, was produced, with a target size of 100 nm or 200 nm.

The composition of the batch is shown in Table 27. The starting material was prepared at 20 gram scale and stirred at 60° C. for 90 minutes. The batch was then extruded at 60° C., 3 times through a 400 nm membrane, and 3 times through a 200 nm membrane. Half of this batch was kept as the 200 nm liposome Formulation 14, and the remaining half was extruded a further 7 times through an 80 nm membrane to produce 100 nm liposome Formulation 15. The samples were stored at 5° C.

TABLE 27

Composition of 5 mg/mL prednisolone liposomes

| | Formulation ID: Formulation 14 and 15 | | |
|---|---|---|---|
| Material | % | Target mass (g) | Actual mass (g) |
| PBS | 88.36 | 21.21 | 22.31 |
| POPC | 12 | 2.88 | 2.8804 |
| Prednisolone | 0.5 | 0.12 | 0.1227 |

Formulation 14 and 15 were stored at 5° C. and tested for total prednisolone content at T=0, and before and after filtering after 1 week. Results are summarized in Table 28. Impurities associated with prednisolone degradation remained at 1.3% of area by HPLC at each time point.

TABLE 28

Prednisolone content in liposome formulations 14 and 15

| | | Prednisolone content (mg/mL) | | |
|---|---|---|---|---|
| Sample ID | Description | T = 0 | T = 1 week | T = 1 week (filtered) |
| Formulation 14 | 5 mg/mL prednisolone liposomes, 200 nm | 5.040 | 5.024 | 4.905 |
| Formulation 15 | 5 mg/mL prednisolone liposomes, 100 nm | 5.182 | 5.172 | 5.156 |

Stability of vesicle size was evaluated by DLS, at T=0, and after 1- and 3-weeks storage at 5° C. Results are presented in Table 29.

TABLE 29

Size stability of liposome Formulations 14 and 15

| | | Average size, nm, and (polydispersity index, %) | | | |
|---|---|---|---|---|---|
| Sample ID | Description | T = 0 | T = 1 Week | T = 1 Week (filtered) | T = 3 Weeks |
| Formulation 14 | 5 mg/mL prednisolone liposomes, 200 nm | 207.8 (23.6) | 204.5 (22.1) | 201.3 (24.3) | 204.4 (24.0) |
| Formulation 15 | 5 mg/mL prednisolone liposomes, 100 nm | 96.86 (17.0) | 100.85 (13.9) | 98.93 (13.9) | 98.29 (18.7) |

Conclusions

The liposomes exhibited physically stability after storage for 3 weeks, as assessed by vesicle size.

Example 5: Prednisolone POPC Liposomes Release Study

Release studies were carried out by sealing a 1 mL sample of the liposomes in a section of cellulose dialysis tubing (Sigma D9277, average molecular weight cutoff 14,000), and immersing in PBS, pH 6.7, at the selected temperature. The samples were stirred using a magnetic stirrer. The solution was sampled at the specified time points and assayed for prednisolone content. At the 24 hour timepoint, the PBS was replaced to maintain sink conditions. The cumulative total amount of prednisolone released was calculated at each timepoint and plotted (as a percentage of the total prednisolone in the sample).
Release of Prednisolone from POPC Liposomes with or without Cholesterol at 37° C.

Samples of prednisolone liposomes (Formulation 10) and prednisolone liposomes with cholesterol (Formulation 11) were assessed in a release study over 3 days at 37° C. Data are shown in FIG. 1.
Release of Prednisolone from 100 nm and 200 nm POPC Liposomes at 32° C.

Figure 2:
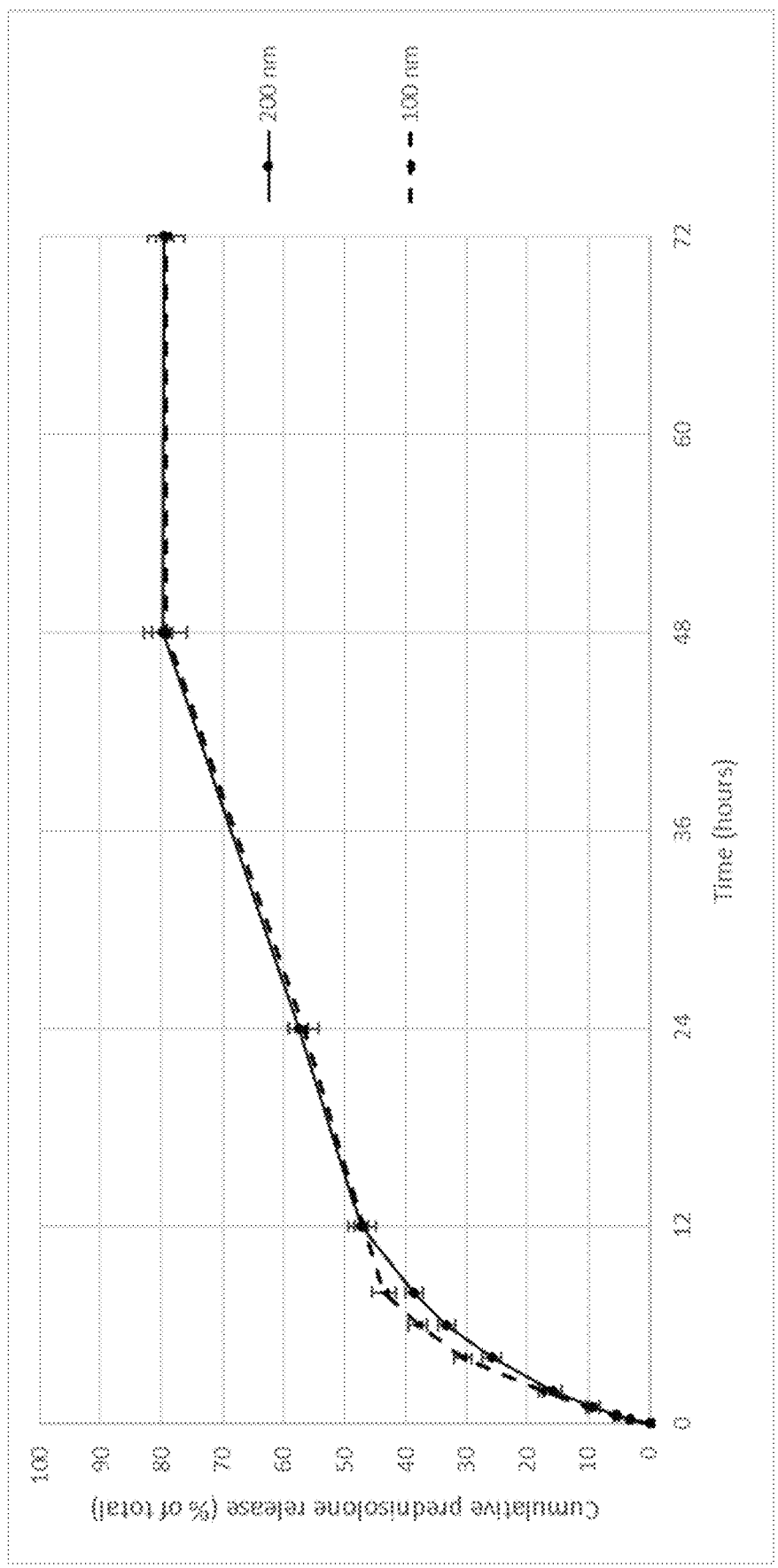
FIG. 2 shows release of prednisolone from 200 nm and 100 nm POPC liposomes at 32° C., 72 hours.

The 5 mg/mL prednisolone POPC liposomes at 200 nm and 100 nm size (Formulation 14 and Formulation 15) were evaluated in a release study at 32° C., over 72 hours, in triplicate. Data are shown in FIG. 2.

The release studies indicated that release of prednisolone from liposomes, with or without cholesterol, or from liposomes of 100 or 200 nm diameter, was similar.

Example 6: Prednisolone Release from POPC Liposome Carrier Compared to DPPC Liposome Carrier The objective of this experiment was to assess the release profile for prednisolone liposomes containing DPPC in comparison to prednisolone liposomes containing POPC. The composition of this formulation, Formulation 16, which contains DPPC, is outlined in Table 30. The batch was prepared at 10 gram scale, at a temperature of 60° C. The target vesicle size was 100 nm. The batch was extruded at a temperature of 60° C., 2 times through a 400 nm membrane, then 9 times through an 80 nm membrane. The sample was stored at 5° C. after extrusion.

TABLE 30

Composition of 5 mg/mL prednisolone DPPC liposomes

| Material | % | Formulation ID: Formulation 16 | |
|---|---|---|---|
| | | Target mass (g) | Actual mass (g) |
| PBS | 92.76 | 11.13 | 11.16 |
| DPPC | 8 | 0.96 | 1.03 |
| Prednisolone | 0.1 | 0.012 | 0.01296 |

Formulation 16 was stored at 5° C. and was analyzed by HPLC for prednisolone and DPPC content (see HPLC methods: DM60, prednisolone drug release; and DM62, DPPC content, respectively), after filtering through a 0.2 μm syringe filter, after 12 days. Results are shown in Table 31.

TABLE 31

Prednisolone content in liposome Formulation 16

| Sample ID | Description | DPPC content (mg/mL) | Prednisolone content (mg/mL) |
|---|---|---|---|
| Formulation 16 | 1 mg/mL prednisolone DPPC liposomes | 92.60 | 1.089 |

Vesicle size was measured for Formulation 16, initially, and after storage at 5° C. for 4 days. Results are shown in Table 32.

TABLE 32

Vesicle size Formulation 16

| Sample ID | Description | Average size, nm (PDI, %) at T = 0 | Average size, nm (PDI, %) at T = 5 days |
|---|---|---|---|
| Formulation 16 | 1 mg/mL prednisolone DPPC liposomes | 98.88 (12.3) | 144.56 (21.2) |

Release Study

Figure 3:
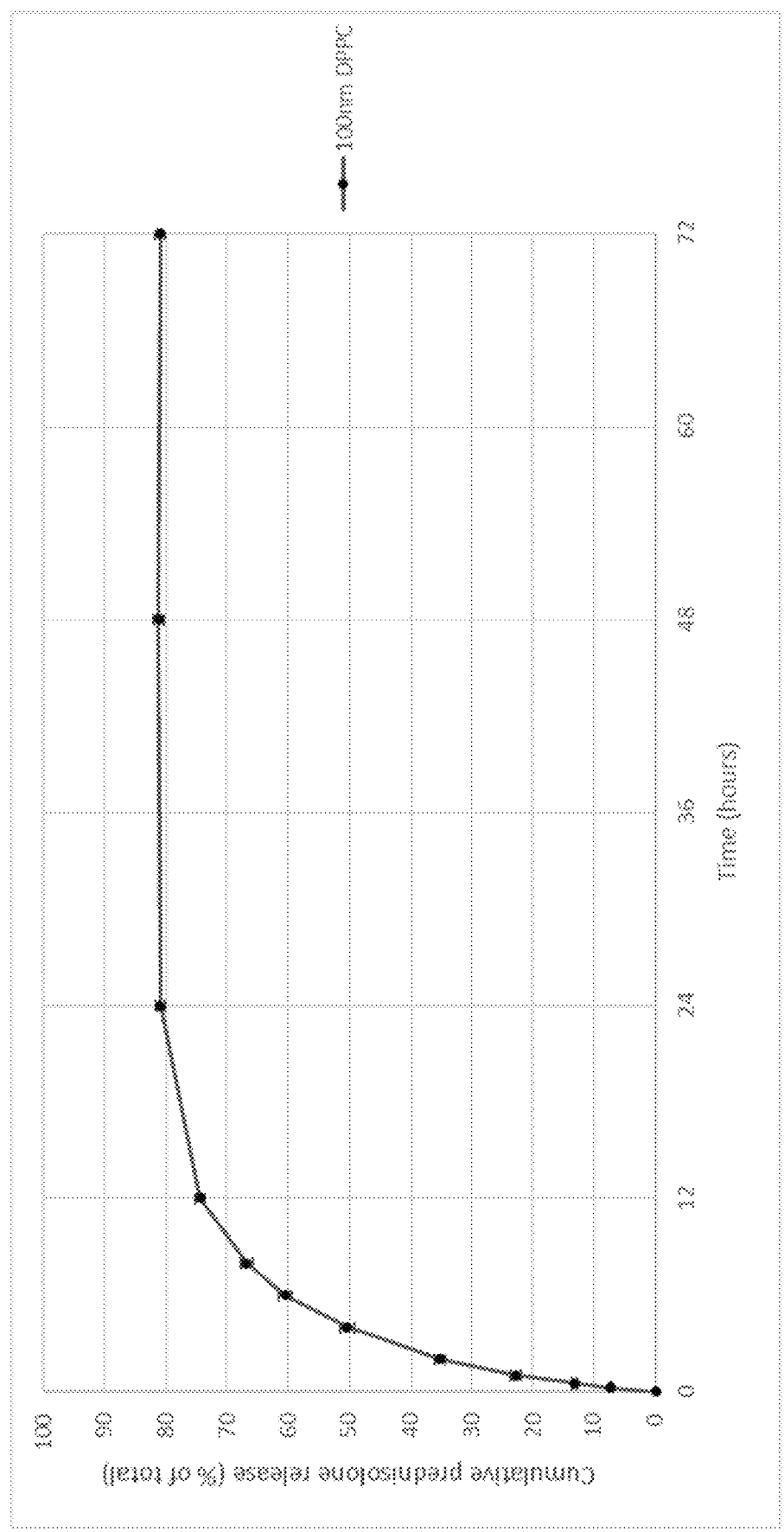
FIG. 3 shows release of prednisolone from 100 nm DPPC liposomes at 32° C., 72 hours.

The 1 mg/mL prednisolone DPPC liposomes Formulation 16 was evaluated in a release study at 32° C., over 72 hours, in triplicate. Data are shown in FIG. 3.

Conclusions

Liposomes with the saturated lipid, DPPC, were produced with 1 mg/mL prednisolone. However, the liposomes appeared not to be as physically stable as the POPC prednisolone liposomes, with an increase in average vesicle size after storage at 5° C. for 5 days.

Figure 4:
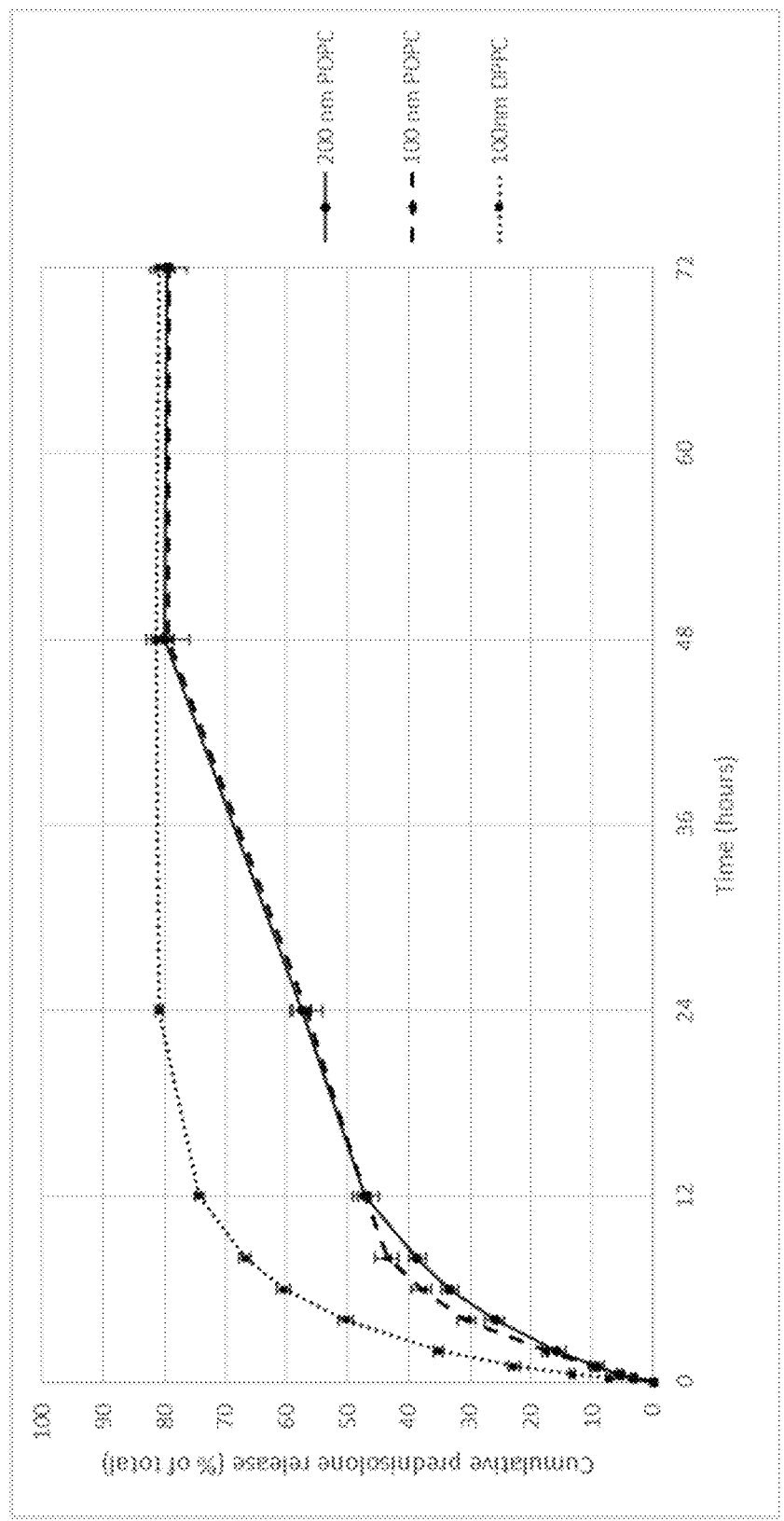
FIG. 4 shows an overlay of the release of prednisolone from 100 nm DPPC liposomes compared to 200 nm and 100 nm POPC liposomes. The DPPC liposomes released prednisolone with an entirely different release profile compared to POPC liposomes. The DPPC release profile shows about 75% release by 12 hours, and about 80% release, the maximal amount, by 24 h. In contrast, the release profile of the POPC liposomes, regardless of size, showed a delayed profile wherein about 55% or less of prednisolone is released at about 12 hours, about 65% or less prednisolone is released at about 24 hours, and about 75% or less is released at about 36 hours.

The drug release profile from the DPPC liposomes was substantially faster compared to the release profile from the POPC liposomes, with maximal release reached within the first 24 hours. Data shown in FIG. 4.

These drug release studies demonstrated that the POPC formulation provided a more sustained release of the drug over the first 48 hours, compared to the DPPC formulation. The DPPC formulations provide a very rapid release, achieving maximal release (~80%) by 24 hours. Such a release profile is not desirable for the disclosed treatments. This is in contrast to the desirable profile achieved with the POPC liposomes.

Example 5: Prednisolone DOPC Liposomes Release Study

Release of Prednisolone from POPC Liposomes with or without Cholesterol at 37° C.

Liposomes were prepare as described above. Briefly, DOPC (120 mg/mL) and prednisolone (5 mg/ml) were combined in solvent, evaporated to dryness, and the resulting film was resuspended in PBS. See Table 31, Formulation 17. The batch was prepared at 10 gram scale, at a temperature of 60° C. The target vesicle size was 100 nm. The batch was extruded at a temperature of 60° C., 3 times through a 400 nm membrane, 3 times through a 200 nm membrane, then 6 times through an 80 nm membrane. The sample was stored at 5° C. after extrusion.

TABLE 31

Composition of 5 mg/mL prednisolone DOPC liposomes

| | | Formulation ID: Formulation 17 | |
|---|---|---|---|
| Material | % | Target mass (g) | Actual mass (g) |
| PBS | 88.36 | 8.84 | 8.85 |
| DOPC | 12 | 0.96 | 1.03 |
| Prednisolone | 0.5 | 0.05 | 0.0529 |

Analysis by HPLC showed that the DOPC content was 127.9 mg/mL and prednisolone content was 5.458 mg/mL.

Release of Prednisolone from 100 nm DOPC liposomes at 32° C.

Figure 5:
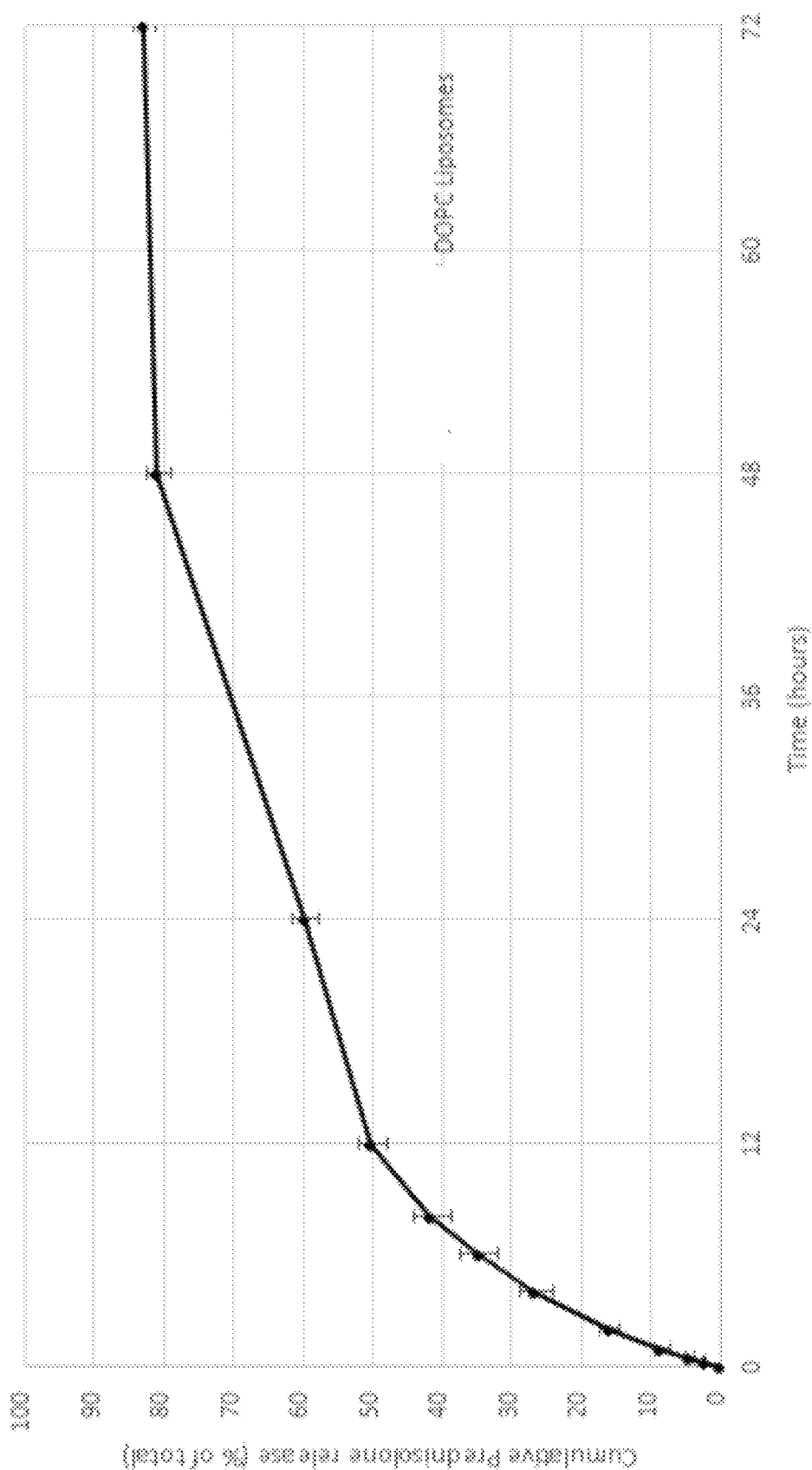
FIG. 5 shows release of prednisolone from 100 nm DOPC liposomes at 32° C., 72 hours. The release profile from the DOPC liposomes has a profile wherein about 55% or less of prednisolone is released at about 12 hours, about 65% or less prednisolone is released at about 24 hours, and about 75% or less is released at about 36 hours.

The 5 mg/mL prednisolone DOPC liposomes at 100 nm size (Formulation 17) were evaluated in a release study at 32° C., over 72 hours, in triplicate. Data are shown in FIG. 5. The data shows that the DOPC liposomes exhibit a desirable release profile where about 50% of prednisolone was released after about 12 hours and about 60% or less prednisolone was released after about 24 hours. Without being bound by theory, it is thought that this release profile provides for an advantageous response in the eye.

The invention claimed is:

1. An ophthalmic composition suitable for ocular injection, comprising
   (i) prednisolone encapsulated in a liposome, wherein the liposome comprises a phospholipid wherein the phospholipid is selected from the group consisting of 1-palmitoyl-2-oleoyl-glycero-3-phosphocholine (POPC)) and 1,2-dioleoyl-sn-glycero-3-phosphocholine (DOPC);
   wherein the liposome has a diameter of about 100 nm to about 200 nm;
   wherein the liposome is free of added cholesterol and free of PEGylated lipid;
   wherein the prednisolone is present at about 3% to about 6% (w/w) of the liposome, and
   (ii) an aqueous buffer suitable for administration to an eye.

2. The ophthalmic composition of claim 1, wherein the aqueous buffer is a phosphate buffered saline (PBS).

3. The ophthalmic composition of claim 1, wherein the phospholipid is DOPC.

4. The ophthalmic composition of claim 1, wherein the phospholipid is POPC.

5. The ophthalmic composition of claim 1, wherein the liposome releases about 55 wt % or less of prednisolone by about 12 hours, about 65 wt % or less prednisolone at about 24 hours, wherein release is determined by HPLC.

6. The ophthalmic composition of claim 1, wherein the liposome releases about 75 wt % or less of prednisolone at about 36 hours, wherein release is determined by HPLC.

7. The ophthalmic composition of claim 3, wherein leakage of prednisolone from the liposome is less than about 10 wt % of prednisolone at 3 weeks when the composition is stored at 5° C.

8. A method of treating a disease or disorder of the eye in a subject in need thereof, comprising injecting the ophthalmic composition of claim 1 into the ocular region.

9. The method of claim 8, wherein the disease or disorder of the eye is selected from the group consisting of: uveitis, diabetic retinopathy, edema, macular degeneration, and telangitis.

10. The method of claim 9, wherein the disease or disorder of the eye is an edema and the edema is a macular edema.

11. The method of claim 10, wherein the macular edema is choroidal macular edema (CME) or diabetic macular edema (DME).

12. The method of claim 8, wherein subject has post ocular surgical inflammation of the eye.

13. The method of claim 8, wherein the injection is subtenon, peribulbar, intracameral or suprachoroidal.

14. The method of claim 8, wherein the ophthalmic composition is administered in a volume of about 0.03 mL to about 0.05 mL.

15. The method of claim 8, wherein the subject has a central retinal vein occlusion (CRVO) or a branch retinal vein occlusion (BRVO).

16. The method of claim 9, wherein the disease or disorder of the eye is macular degeneration and the macular degeneration is age related macular degeneration (ARMD).

* * * * *

UNITED STATES PATENT AND TRADEMARK OFFICE
CERTIFICATE OF CORRECTION

PATENT NO. : 12,370,201 B2
APPLICATION NO. : 18/768689
DATED : July 29, 2025
INVENTOR(S) : Subramanian Venkatraman et al.

Page 1 of 1

It is certified that error appears in the above-identified patent and that said Letters Patent is hereby corrected as shown below:

On the Title Page

"(71) Applicant: EDEN Opthalmic PTE Ltd., Singapore (SG)"
Should read:
--(71) Applicant: EDEN Ophthalmic PTE Ltd., Singapore (SG)--

Signed and Sealed this
Sixteenth Day of September, 2025

Coke Morgan Stewart
*Acting Director of the United States Patent and Trademark Office*